United States Patent
Kumar et al.

(10) Patent No.: US 10,408,802 B2
(45) Date of Patent: Sep. 10, 2019

(54) THERMAL CONDUCTIVITY SENSING DEVICE, METHODS FOR OPERATION AND USES OF THE SAME

(71) Applicant: Cambridge Enterprise Limited, Cambridge (GB)

(72) Inventors: Vasant Ramachandran Kumar, Cambridge (GB); Sohab Sarfraz, Cambridge (GB); Florin Udrea, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 134 days.

(21) Appl. No.: 15/529,944

(22) PCT Filed: Nov. 27, 2015

(86) PCT No.: PCT/EP2015/077948
§ 371 (c)(1),
(2) Date: May 25, 2017

(87) PCT Pub. No.: WO2016/086589
PCT Pub. Date: Jun. 2, 2016

(65) Prior Publication Data
US 2017/0363589 A1    Dec. 21, 2017

(30) Foreign Application Priority Data

Nov. 27, 2014 (GB) .................................. 1421102.3

(51) Int. Cl.
*G01N 30/66* (2006.01)
*G01N 25/18* (2006.01)
(Continued)

(52) U.S. Cl.
CPC ............. *G01N 30/66* (2013.01); *G01N 25/18* (2013.01); *G01N 27/18* (2013.01); *G01N 30/6095* (2013.01); *G01N 33/497* (2013.01)

(58) Field of Classification Search
CPC ............................... G01N 30/66; G01N 25/18
See application file for complete search history.

(56) References Cited

U.S. PATENT DOCUMENTS 3,888,110 A * 6/1975 Clark ..................... G01N 27/18
                                                        73/23.4
4,170,126 A * 10/1979 Craven .................. G01N 27/18
                                                        277/637
(Continued)

FOREIGN PATENT DOCUMENTS

EP    2 629 084    8/2013
EP    2645 091    10/2013
(Continued)

OTHER PUBLICATIONS

Agilent (2010) SI-02239 490 Micro GC Solution data sheet 1.
(Continued)

*Primary Examiner* — David A Rogers
(74) *Attorney, Agent, or Firm* — Rudy J. Ng; Bozicevic, Fields & Francis LLP

(57) ABSTRACT

A thermal conductivity sensing device (1) is disclosed, along with a method for operation of the thermal conductivity sensing device and use of the thermal conductivity sensing device in a system for gas chromatography and a method of carrying out gas chromatography. The thermal conductivity sensing device is for use in sensing one or more gaseous components in a flowing gaseous environment. The device has a first sensor (4B) and a second sensor (4A) for exposure to the same flowing gaseous environment (G). The first sensor has an associated flow altering means (20) to affect gas flow at least at part of the surface of the first sensor, to
(Continued)

be different to gas flow at the surface of the second sensor. Each sensor provides an output relating to heat transfer between a surface of the sensor and the gaseous environment. The device is operable to compare outputs of the first and second sensors. The sensor is able to reduce the effects of bulk convection of the flowing gas on thermal conductivity measurements.

16 Claims, 34 Drawing Sheets

(51) Int. Cl.
  *G01N 27/18* (2006.01)
  *G01N 30/60* (2006.01)
  *G01N 33/497* (2006.01)

(56) References Cited

U.S. PATENT DOCUMENTS

| | | | | |
|---|---|---|---|---|
| 4,594,879 | A * | 6/1986 | Maeda | G01N 30/66 |
| | | | | 73/25.03 |
| 5,463,899 | A | 11/1995 | Zemel et al. | |
| 6,010,243 | A * | 1/2000 | Hessler | C12M 41/14 |
| | | | | 374/1 |
| 6,361,206 | B1 * | 3/2002 | Bonne | G01F 1/6842 |
| | | | | 374/135 |
| 6,928,858 | B2 * | 8/2005 | Lin | G01N 27/18 |
| | | | | 422/83 |
| 7,021,821 | B2 * | 4/2006 | Bonne | G01N 25/18 |
| | | | | 374/10 |
| 8,302,459 | B2 * | 11/2012 | Matsuhama | G01N 25/18 |
| | | | | 422/83 |
| 9,080,907 | B2 | 7/2015 | Haneef et al. | |
| 9,128,028 | B2 * | 9/2015 | McBrady | G01N 30/66 |
| 2005/2065422 | | 12/2005 | Bonne | |
| 2009/0193872 | A1 * | 8/2009 | Tokuda | G01N 25/18 |
| | | | | 73/23.31 |
| 2010/0242573 | A1 | 9/2010 | Matsuhama et al. | |
| 2010/0294021 | A1 * | 11/2010 | Makino | G01N 25/18 |
| | | | | 73/25.03 |
| 2012/0024043 | A1 * | 2/2012 | McBrady | G01N 27/18 |
| | | | | 73/25.03 |
| 2013/0256825 | A1 | 10/2013 | Humbert et al. | |
| 2014/0177673 | A1 * | 6/2014 | Bliss | G01N 25/18 |
| | | | | 374/165 |
| 2014/0373621 | A1 * | 12/2014 | Schirm | G01F 1/6965 |
| | | | | 73/204.11 |
| 2015/0052974 | A1 * | 2/2015 | Pieczarek | G01N 25/18 |
| | | | | 73/25.03 |
| 2015/0219578 | A1 * | 8/2015 | Gellert | G01N 27/18 |
| | | | | 73/25.03 |

FOREIGN PATENT DOCUMENTS

| | | |
|---|---|---|
| GB | 785074 | 6/1955 |
| GB | 1356334 A * | 6/1974 |
| JP | 2001-337058 A * | 12/2001 |
| WO | WO 9919050 | 4/1999 |
| WO | WO 2005119232 | 12/2005 |
| WO | WO 2011044547 | 4/2011 |
| WO | WO 2014006648 | 1/2014 |

OTHER PUBLICATIONS

Ali (2008) "Tungsten-Based SOI Microhotplates for Smart Gas Sensors," Journal of Microelectromechanical Systems 17(6): 1408-1417.
Brand et al., (2008) "Fabrication Technology," CMOS Technology 1 ed.: 596.
GB1421102.3 (2015) Search Report under Section 17(5) 1-4.
Herwaarden (2010) "Thermal Conductivity Gauge," Xensor Integration 1-22 XEN-TCG3880.
Kaanta et al., (2011) "Effect of forced convection on thermal distribution in micro thermal conductivity detectors," J. Micromech. Microeng 21: 1-8 045017 (8pp).
Kaanta et al., (2010) "Novel device for calibration-free flow rate measurements in micro gas chromatographic systems," J. Micromech. Microeng 20: 1-7 095034 (7pp).
Kaanta et al., (2011) "Temperature distribution on thermal conductivity detectors for flow rate insensitivity," Sensors and Actuators A 167: 146-151.
PCT/EP2015/077948 (2016) ISR 1-15.
Rastrello et al., (2012) "Thermal Conductivity Detector for Gas-Chromatography: Acquisition System and Experimental Measurements," IEEE International 1226-1230.
Rastrello et al., (2013) "Thermal Conductivity Detector for Gas Chromatography: Very Wide Gain Range Acquisition System and Experimental Measurements," IEEE Transactions on Instrumentation and Measurement 62(5): 974-981.
Romero et al., (2013) "Sensors and Actuators A: Physical," Sensors and Actuators A 203: 225-231.
Sarfraz et al., (2013) "A Dual Mode SOI CMOS MEMS based Thermal Conductivity and IR Absorption Gas Sensor," IEEE pp. 1,4,3-6.
SEVCIK (1976) "Detectors in Gas Chromatography," 192.

* cited by examiner

See Fig. 7

THERMAL CONDUCTIVITY SENSING DEVICE, METHODS FOR OPERATION AND USES OF THE SAME

CROSS-REFERENCE TO RELATED APPLICATIONS

This application is the U.S. national phase under 35 U.S.C. § 371 of PCT International Application No. PCT/EP2015/077948, which has an international filing date of Nov. 27, 2015 and designated the United States of America, which application claims benefit of priority to GB Application No. 1421102.3, filed Nov. 27, 2014, the disclosures of each of which are incorporated by reference herein.

BACKGROUND TO THE INVENTION

Field of the Invention

This invention relates to a thermal conductivity sensing device, to a method for operation of the thermal conductivity sensing device and to uses of the thermal conductivity sensing device. The invention is of particular interest as a sensor in a gaseous environment, for sensing thermal conductivity of the gaseous environment which can provide information on the gas components. The invention has particular, but not exclusive, applicability in the fields of gas chromatography and/or medical analysis.

Related Art

Gas chromatography is a technique which is used to separate and detect the components of a mixture of gases. Gas chromatography is typically carried out using a separation column. The gas mixture to be separated into its constituent components is carried through the column using a carrier gas ('mobile phase'). The column is provided with a stationary phase (e.g. a coating on an inner surface of the column). The stationary phase retards the different components of the gas mixture to different extents, in a conventionally-known manner. As a result, the different components are passed through the separation column at different rates, and elute from the column at different, characteristic times, known as retention times.

As the separated components elute from the column, a detector presented to the gas flow detects the components eluted from the column. Suitable detectors are known which detect the thermal conductivity of a gaseous environment. These are referred to in the art as thermal conductivity detectors (TCDs). These rely on the fact that different gas components have different thermal conductivities, and in particular, a different thermal conductivity from the mobile phase. As one component reaches the detector, the change in thermal conductivity of the gaseous environment registers as a peak. The change in thermal conductivity of the gaseous environment, along with the retention time, can then be used to identify the component.

One benefit of TCDs is that they do not rely on any kind of chemical reaction. They are able to detect not only the presence of the different components in the environment, but given the identity of the expected components, they can also provide information related to the concentration of the components.

The basic operating principle of a typical known TCD is to have a heated filament located to be in thermal contact with a gaseous analyte. A change in composition of the analyte typically changes the thermal conductivity of the analyte. Therefore the rate at which the heated filament loses heat to the analyte also changes, resulting in a change in temperature of the heated filament. This change in temperature is usually measured as a change in electrical resistance of the heated filament. A well-known example of a device which relies on thermal conductivity to measure low gas pressures is a Pirani gauge, which has a heated filament exposed to the gas. The lower the pressure, the lower the rate of heat loss to the surroundings. Therefore, by measuring the temperature of the filament, one can infer the gas pressure (i.e. the extent of the vacuum).

As mentioned above, TCDs can be used in gas chromatography, but can also be used in sensors for any mixture of gases, for example hydrogen and natural gas, or air and fuel in combustion systems.

Thermal conductivity gauge XEN-TCG3880 of Xensor Integration by (Distributieweg 28, 2645 EJ Delfgauw, Netherlands, www.xensor.nl) is a commercially-available sensor. It is a thin-film-thermopile TCD. The device has a heated membrane in contact with hot junctions of the thermopile. The cold junctions are connected to the thick rim of the chip.

WO 2011/044547 discloses a micro-TCD which is made up of a chamber with a suspended heater inside, with current contacts and voltage contacts. In one embodiment, there is a series of three heating elements located along the gas flow path. An analyte band flowing along the gas flow path is detected by the first element and subsequently by the second and third, the delay between the detection by each element providing a measure of the flow rate.

Kaanta et al. (2010) and Kaanta et al. (J. Micromech. Microeng 2011) discuss a sensor which utilizes thermal conductivity measurements to infer the flow rate of a sample gas within a detector. This device consists of several detector elements, which are all heated and measured simultaneously. This allows for direct measurement of the sample peak as it progresses through the microchannel of the detector. This works by maintaining the heated filament at a constant temperature, and monitoring the power required to maintain the temperature. The lower the power, the lower the thermal conductivity of the sample. The feedback system required to maintain the constant temperature is provided by having the micro-TCD connected as one of the four components of a Wheatstone bridge.

Rastrello et al. (2012) and Rastrello et al. (2013) disclose a micromachined TCD. Here, two pairs of identical platinum resistors are arranged into a Wheatstone bridge defined over suspended dielectric membranes. One arm of the bridge is designated a reference channel, and the second arm is designated an analytical channel. During use, the analytical channel receives the gas flow output of a gas chromatography column and the reference channel is connected to an empty fused silica capillary or to the carrier gas only.

US 2013/0256825 A1 discloses an integrated circuit which comprises a gas sensor. The sensor described in this document features an electrically resistive sensor element which is located in a position where it is exposed to the sample gas. The circuit also includes a barrier, which forms a trench for the sensor to sit inside, with the intention of inhibiting detrimental effects caused by exposing the sensor directly to the flowing gas.

Romero et al. (2013) discuss a calorimetric method for a combination of flow rate and thermal conductivity measurements. Calorimetric flow sensors usually feature a heater and two temperature sensors, up- and downstream of the heater, with the temperature difference between the sensors indicative of the flow velocity. In this paper, the thermal conductivity is measured by generating heat sinusoidally, at a fixed frequency, allowing the measurements to be made without prior knowledge of the rate of flow. The device can also measure the flow rate of the gas in a DC mode, if the thermal diffusivity of the gas is known.

SUMMARY OF THE INVENTION

A problem which affects some known TCDs is their vulnerability to the effects of the flow of a gas over them. When located in a flowing gaseous environment, heat is transferred not only by conduction through the gas, but also advection due to the bulk motion of the gas itself. Many of the known devices discussed above rely on an assumption that the effect of gas thermal conduction is dominant. However, there are many situations in which this assumption does not hold, both in fast-flowing and slow-flowing gas flow paths. This can lead to incorrect thermal conductivity measurements, because heat loss into the gas also includes a substantial contribution from the advective effects of the gas flow.

The flow of gas in many applications can be highly nonlinear, and can be strongly dependent on variables such as temperature and pressure. As a result, accurately modelling the fluid dynamics of the system in order to account for the advective heat loss effect is extremely complex.

It is of interest in relation to the present invention to investigate gaseous environments which include naturally occurring gases (i.e. permanent gases) and/or volatile organic compounds. It is considered that known gas chromatography systems are susceptible of further improvement. It is further considered that there is an unmet need in the field of medical diagnostic equipment, for example in relation to analysis of breath, to provide information on the composition of breath for diagnostic purposes.

The present invention has been devised in order to address at least one of the above problems. Preferably, the present invention reduces, ameliorates, avoids or overcomes at least one of the above problems.

The present inventors have realised that it is possible to reduce the effect of the flow on thermal conductivity measurements by providing two different sensors in the same gaseous environment, and comparing the outputs of the two sensors.

In a general aspect of the invention, the present invention compares the outputs of two sensors in the same gaseous environment, the first sensor having an associated flow altering means to affect gas flow at least at part of the surface of the first sensor for thermal contact with the gaseous environment, to be different to gas flow at the surface of the second sensor, the device being operable to compare outputs of the first and second sensors.

Accordingly, in a first preferred aspect, the present invention provides a thermal conductivity sensing device for use in sensing one or more gaseous components in a flowing gaseous environment, the device having a first sensor and a second sensor for exposure to the gaseous environment, each sensor providing a surface for thermal contact with the gaseous environment, each sensor providing an output relating to heat transfer between said surface and the gaseous environment, the first sensor having an associated flow altering means to affect gas flow at least at part of said surface of the first sensor, to be different to gas flow at the surface of the second sensor, the device being operable to compare outputs of the first and second sensors.

In a second preferred aspect, the present invention provides a method for measuring the thermal conductivity of one or more gaseous components in a flowing gaseous environment, the method including:

exposing a surface of a first sensor to the flowing gaseous environment, for thermal contact between the first sensor and the gaseous environment;
generating a first output relating to heat transfer between said surface of the first sensor and the gaseous environment;
exposing a surface of a second sensor to the same flowing gaseous environment, for thermal contact between the second sensor and the gaseous environment;
generating a second output relating to heat transfer between said surface of the second sensor and the gaseous environment;
comparing the outputs of the first and second sensors;
wherein the first sensor has an associated flow altering means to affect gas flow at least at part of said surface of the first sensor, to be different to gas flow at the surface of the second sensor.

In a third preferred aspect, the present invention provides a system for performing gas chromatography, the system including:

a separation column (or micro-column) with a gas inlet and a gas outlet, the separation column being provided with a stationary phase, and
a thermal conductivity sensing device according to the first aspect to receive a gas flow in the separation column or from the outlet of the separation column.

It is possible to place the thermal conductivity sensing device inside the column (or micro-column) or be part of the column (or micro-column). This allows the performance of in situ measurements, which is not possible where the device is located at the outlet of the column. In situ measurement provide additional information about the chemical species in the sample and also information about the working principles and internal conditions of the column (or micro-column).

In a fourth preferred aspect, the present invention provides use of the thermal conductivity sensing device of the first aspect in gas chromatography.

In a fifth preferred aspect, the present invention provides a method of carrying out gas chromatography, the method including the steps:

separating one or more gas components from a gas carrier mobile phase using a separation column (or micro-column);
providing a gas flow to a thermal conductivity sensing device according to the first aspect, located in the column, or directing a gas flow to a thermal conductivity sensing device according to the first aspect from the outlet of the separation column; and
comparing the outputs of the first and second sensors of the thermal conductivity sensing device.

In a sixth preferred aspect, the present invention provides a system for analysis of breath, the system being operable to receive a sample of breath from a subject, the system including a thermal conductivity sensing device according to the first aspect arranged to sense one or more gaseous components in a gaseous environment formed at least in part by said sample of breath.

In a seventh preferred aspect, the present invention provides use of the thermal conductivity sensing device of the first aspect in analysis of breath.

In an eighth preferred aspect, the present invention provides a method of carrying out breath analysis, the method including the steps:

directing a sample of breath from a subject to a thermal conductivity sensing device according to the first aspect; and comparing the outputs of the first and second sensors of the thermal conductivity sensing device.

In some embodiments, the eighth preferred aspect excludes a diagnostic step. This may be the case in particular where the sample of breath is breathed into a system incorporating said thermal conductivity sensing device.

In the sixth, seventh and/or eighth aspects, the sample of breath may be provided directly to the system by the subject. Alternatively, the sample of breath may be stored in a storage means for subsequent introduction into the system.

The first, second, third, fourth, fifth, sixth, seventh and/or eighth aspects of the invention may be combined with each other in any suitable combination unless the context demands otherwise.

The first, second, third, fourth, fifth, sixth, seventh and/or eighth aspects of the invention may have any one or, to the extent that they are compatible, any combination of the following optional features.

Preferably, the first and second sensors are provided with respective heating elements. In operation of the device, heat is typically transferred from the first and second sensors to the gaseous environment. The output of the first and second sensors may be a measure of resistance—across the respective heating elements. The resistance of the heating elements typically changes with temperature. The heating elements may be formed using, for example, a positive temperature coefficient material. A particularly suitable material is a refractory metal such as tungsten or a tungsten-based alloy, which does not suffer from potentially problematic electromigration effects. Other metals which may be used for the heating elements include, but are not limited to copper, aluminium, nickel, titanium, platinum, palladium, gold and molybdenum. Such materials are suited to known MEMS (Micro Electro-Mechanical Systems) manufacturing processes. Other materials can be used, for example polysilicon. Preferably, the heating elements of the first and second sensors are substantially identical.

The outputs from the first and/or second sensors can be determined based on a Wheatstone bridge arrangement.

There are two suitable modes of operation for each of the sensors. In one mode, the heating element of the sensor can be held with a constant voltage across it or a constant current through it, the temperature change of the heating element being determined. In another mode, the heating element can be maintained at a constant temperature, and the change in power required to maintain this temperature can be determined, since the power supplied to the heating element corresponds to the power lost to the gas when the heating element remains at a constant temperature.

Preferably, for each sensor, the heating element is embedded. The structure in which the heating element is embedded preferably provides the surface for thermal contact with the gaseous environment. Preferably the material in which the heating element is embedded protects the heating element from corrosion, oxidation or other degradation in the gaseous environment. In this way, the sensors can operate at high temperature, which is advantageous for sensitivity of thermal conductivity measurements, and enhancement of the reliability of the sensors.

The surface for thermal contact with the gaseous environment is therefore preferably not a surface of a heating element. Preferably, the associated flow altering means to affect gas flow at least at part of said surface of the first sensor comprises one or more features of the surface of the first sensor. The structure in which the heating element is embedded can be formed in a suitable shape to provide such features.

Preferably, for each sensor, the heating element is embedded in a membrane. This provides an arrangement with low heat capacity, allowing fast response time. Furthermore, use of SOI (Silicon-On-Insulator) technology during fabrication of the membrane, means that the membrane can be fabricated along with diode- or thermopile-based temperature sensors to monitor the change in temperature of the heating element in addition to temperature sensing by measuring the electrical resistance of the heater itself.

The membrane may be formed with a constant depth across its area. Where the membrane has a constant depth across its area, the membrane may have a depth of at most 25 µm, more preferably at most 10 µm, and more preferably at most 5 µm. Depths of 5 µm can be achieved using CMOS (Complementary Metal Oxide Semiconductor) processes and SOI wafers.

As explained below, in some embodiments at least for the first sensor, the membrane may have non-constant depth across its area. In such embodiments, it is possible to consider the maximum depth of the membrane across its area, and the minimum depth of the same membrane across its area. Here, the membrane may have a maximum depth of at most 25 µm, more preferably a maximum depth of at most 10 µm, and more preferably still a maximum depth of at most 3 µm. The membrane may have a minimum depth of at least 2.0 µm.

Thin membranes have several advantages in the present invention. Thin membranes provide fast sensor response time. Thin membranes have low heat capacity and so can be heated quickly to operating temperature. The provision of a membrane also provides thermal isolation between the sensor and the processing electronics.

The membrane preferably has at least one lateral dimension of at most 2000 µm, more preferably at most 1000 µm more preferably at most 500 µm, still more preferably at most 100 µm, still more preferably at most 50 µm, and still more preferably at most 20 µm. In some embodiments, the membrane may be substantially equi-axed in length and width (i.e. the length and width of the membrane may be substantially the same). In other embodiments, the membrane may have an aspect ratio (ratio of length to width) of at least 2, or at least 5. The area of the membrane may be at least 0.001 mm². This is satisfied for example by a membrane with width at least 20 µm and length at least 50 µm. The area of the membrane may be at most—4 mm². This is satisfied for example by a membrane with width at most 2000 µm and length at most 2000 µm. Preferably the area footprint of the heater element corresponds to or is smaller than the area footprint of the membrane.

Preferably, the first and second sensors are situated in a channel, configured so that gas flowing along said channel is in contact with the surface for thermal contact with the gaseous environment. The channel may have a wall which opposes the sensor surface. The present inventors have found that the distance between the channel wall and the sensor surface has an effect on the sensitivity of the device to gas flow. This depends to some extent on the gas flow velocity, but an aim of the present invention is to reduce the sensitivity of the device to gas flow, as shown in FIG. 12, which is discussed in greater detail later. In order to reduce this sensitivity, preferably the distance between the sensor surface and the channel wall is at most 10000 µm, more preferably 5000 µm, more preferably 1000 µm, more preferably at most 500 µm, more preferably at most 100 µm, still more preferably at most 50 µm, and most preferably, at most 10 µm. For applications such as breath analysis, the distance between the sensor surface and the channel wall may be relatively large, e.g. in the range 500-10000 μm.

Preferably, other than the flow altering means to affect gas flow at least at part of said surface of the first sensor, the first and second sensors are substantially identical. This allows the signals from the two sensors to be compared with confidence, with any difference attributable mainly or totally to the effect of the flow altering means.

Preferably, in use, the first and second sensors are exposed to the same gaseous environment at substantially the same time. This is different from arrangements in which sensors are arranged spaced apart along a flow path in order to detect the flow rate of gas components in the flowing gas stream, the aim of the preferred embodiments of the present invention being to reduce or eliminate the effect of gas flow on the measurement of thermal conductivity.

The sensors preferably have a centre-to-centre spacing of at most 3000 μm, and more preferably at most 2000 μm, more preferably at most 1500 μm. In yet further miniaturised embodiments, preferably the centre-to-centre spacing is at most 1000 μm, more preferably at most 500 μm, more preferably at most 300 μm, more preferably at most 100 μm, and more preferably at most 50 μm. The centre-to-centre spacing is preferably measured based on the centre of the respective heating element footprint and/or centre of the respective membrane footprint.

The thermal conductivity sensing device preferably has the first and second sensors formed in a fixed position relative to each other. The first and second sensors may form part of an integral device. For example, the first and second sensors may be formed on a single chip. This allows the device to be compact and spaced apart at a precise distance. This is advantageous for example for micro gas chromatography systems. Knowledge of the precise distance also allows determination of gas flow velocity.

Most preferably, this device is formed using CMOS techniques. This manufacturing technique confers many advantages. CMOS techniques use industry standard processes for fabrication of microstructures and are therefore readily repeatable. By using the metal and inter-metal dielectric layers of the CMOS process, the physical sensor and the sensor drive and signal processing electronics can reside side by side on the same physical chip. This small distance separating the electronics and sensor results in a reduction or avoidance of parasitic signals arising from transmission line inductance and capacitance. The CMOS process is highly mature and repeatable—this means that the material properties are tightly controlled, which further reduces or avoids parasitic signals. Chips fabricated using the CMOS process are able to benefit from the reliability, capacity and economies of scale of the global semiconductor market. Therefore, using CMOS techniques leads to an overall reduced system size while simultaneously addressing manufacturing costs and reliability issues.

When the device is manufactured using CMOS processes, the heating element may include copper, aluminium, tungsten or titanium, these materials being acceptable in CMOS fabrication lines. The heating element may also include polysilicon, which is readily used in CMOS processes.

Preferably, the flow altering means includes a recess in the surface of the first sensor. In operation, when the gas is flowing over the surface, a small amount of gas is effectively trapped in the recess. When the gas to be subject to detections is travelling at an appropriate speed (dependent on the dimensions of the recess) with respect to the dimensions (length in the gas flow direction and depth), the streamlines of the gas flowing over the recess substantially do not enter the recess, leaving a region of gas inside the groove substantially unaffected by the flow of the gas, either stagnating or swirling in trapped vortices which are isolated from the main streamlines. The composition of the gas trapped in the recess is then diffusion-limited, i.e. gas atoms or molecules may enter and exit the recess substantially by diffusion only. As a result of this, the heat transfer from each sensor due solely to the flow of the gas will be substantially identical, so a comparison of the heat loss between the two will enable this contribution either to be removed or greatly suppressed, leaving only the contribution from the thermal conductivity of the gas in the groove. This leads to a thermal conductivity measurement which is substantially flow-invariant.

An array of recesses may be provided. Preferably these are substantially identical in shape. Preferably the recesses are provided in an ordered array, such as a periodic array. This allows for greater predictability of performance of the device in different conditions, for example by numerical modelling.

Preferably the array of recesses extends to cover the footprint of the heating element at least.

Each recess may be provided for example by a groove or by a hole. An interconnected array of grooves or holes may be provided. This may have the advantage, as explained below, of making the device substantially flow direction invariant. As will be understood, grooves and holes are typically formed by a subtractive process. The recesses may alternatively be provided by an additive process, e.g. by growing, depositing and/or patterning pillars, tubes or islands as required.

In some preferred embodiments, the recess is a groove. Preferably, the groove extends in a direction substantially transverse to the gas flow direction. There is no particular limit on the extent of the groove in this direction, although preferably the groove extends to cover the footprint of the heating element at least.

In some embodiments, it is advantageous for the device to be substantially gas flow direction invariant. This may be useful for example where the orientation of the device with respect to the gas flow is not known or fixed. It may be of particular use where the flowing gaseous environment includes at least some regions of turbulent flow.

Where the recesses are straight grooves directed transverse to the gas flow direction, the device is sensitive to gas flow in a particular direction, which would be along the direction of the grooves. However, this may be advantageous where a fast response time is required, since the grooves will be refreshed with the new gaseous environment quickly. Provision of grooves in different directions (e.g. arrayed as a grid) can provide both advantages. Orientation of the grooves to be non-parallel (e.g. directed at an angle of at least 30°) to the gas flow direction can be particularly advantageous.

In some embodiments, the grooves may be non-linear, in the sense of describing a non-straight line. The grooves may be curved, kinked, meandering, zig-zagged, etc. This assists in providing flow direction invariance and faster sensor response to changing gaseous species.

In a similar manner, where the recesses are holes, it is possible to provide flow direction invariance by ensuring that there is no continuous flow path available for gas to flow along the recesses, independent of the gas flow direction.

In some embodiments, a combination of grooves and holes may be provided.

The recess may have a substantially rectangular cross section when viewed along an axis perpendicular to the direction of gas flow. Alternatively the recess may have a trapezoidal cross section when viewed along an axis perpendicular to the direction of gas flow. In this case, the recess may have a narrower base than opening, or a narrower opening than base. The side walls of the recess may subtend the same angle or different angles with the major plane of the device. In the direction of the gas flow, the length of the recess is preferably at most 20 μm, more preferably at most 13 μm, more preferably at most 10 μm, more preferably at most 7 μm, more preferably at most 4 μm, more preferably at most 3 μm, more preferably at most 2 μm, more preferably at most 1 μm and most preferably at most 0.5 μm. These consideration apply to grooves and/or holes. There may additionally be provided sub-recesses within a main recess. The sub-recesses may have dimensions within the ranges given above, with the main recesses having dimensions also within the ranges given above, but larger than for the sub-recesses.

Thus, in a preferred embodiment, the device has a plurality of grooves in the surface of the first sensor. These may be parallel. Alternatively, where the grooves are set at a non-zero angle to each other, this can help to increase sensor response with respect to one type of gas molecules exiting the grooves while others enter. As mentioned above, there may additionally or alternatively be provided recesses in other forms, such as holes.

The presence of more than one recess means that a correspondingly large proportion of the membrane will be sensitive to the thermal conductivity of the gas, since the sensor operates by changing the effective thermal conductivity of the membrane by filling the grooves with analyte gas. A differential measurement then between sensors with and without grooves then represents the true thermal conductivity of the gas: more grooves therefore leads to a better response and sensitivity. In another embodiment of the present invention, the grooves may form a network with a "criss-cross" pattern, with the advantages explained above.

The comparison of the outputs from the two sensors may be in the form of a differential measurement, subtracting the output of the first sensor from that of the second sensor, or vice versa. A thermal conductivity of the gas can be deduced from this.

The heat transfer losses due to convection (conduction plus advection in the fluid above and below the membrane) can be reduced by having a sensor membrane radius to sensor heater radius ratio of less than 1.65. Therefore the heat transfer in preferred embodiments occurs primarily by conduction in the membrane only. There are typically some, though small, losses due to convection in the fluid above and below the membrane and at high temperatures also (even smaller) losses due to IR radiation.

Therefore, in the preferred differential signal measurement, the heat transfer losses due to convection and radiation cancel out. Also in the preferred differential signal, heat transfer losses due to conduction (considering for example now only laterally in the membrane) are a direct indication of the thermal conductivity of the gas molecules trapped in the grooves.

Thus, the preferred differential signal eliminates the common mode error from the two sensors due to:
1. Convection in the fluid stream above and below the membrane
2. Radiation above and below the membrane The preferred differential signal is therefore a direct result of the net effective thermal conductivity of the membrane, which is due to the trapped gas molecules, this varying depending upon the gas entity/entities trapped.

Since the thermal conductivity contribution of a component carried by the carrier gas is dependent only on the concentration of the component, and not the total mass of the component, the device of the preferred embodiments of the invention are ideal for miniaturization, allowing the implementation of portable micro-chromatography systems. This is highly advantageous, since these can be cheaply batch produced, and due to their smaller masses, they have increased mechanical robustness and reduced power consumption.

The sensors may be operated at any suitable operating temperature of interest, depending on the intended application, provided that the temperature is greater than ambient temperature. For example, preferably the sensors are operated at a temperature of at least 50° C. More preferably, the sensors are operated at temperature of at least 100° C., at least 150° C., at least 200° C., at least 250° C. or at least 300° C. Higher operating temperatures are of interest in particular in view of the increased signal-to-noise ratio, in view of heat being lost more quickly from the heater to its environment. The sensors may be operated at a temperature of at most 800° C., more preferably at most 750° C. In typical operation, the sensors may be operated at about 400° C.

At higher operating temperatures, infrared (IR) emission from the sensors becomes significant. This can be used for comparing IR absorption from the sensors (due at least in part to absorption by the gaseous environment) at a first operating temperature which is higher than a second operating temperature. At the second operating temperature, IR emission becomes negligible, and therefore a measurement at the second operating temperature substantially excludes an IR absorption component. In this mode of operation of the sensing device, preferably the second operating temperature is at most 450° C. Suitable lower limits for the second operating temperature are set out above. Preferably the first operating temperature is at most 500° C., more preferably 600° C., still more preferably at least 650° C. Suitable upper limits for the first operating temperature are set out above. For example, a first operating temperature of about 600° C. is considered suitable, being a temperature at which there is substantial IR emission.

Therefore, in one operating mode of the device, measurements are taken at the first operating temperature and at the second operating temperature, and the measurements compared to provide information on IR absorption.

In another operating mode of the device, the device is operated at the first operating temperature (in one of the ranges for the first operating temperature identified above).

Such operation of the device is significant because greenhouse gases such as carbon dioxide ($CO_2$) and methane ($CH_4$) absorb IR radiation while oxygen and nitrogen do not.

The content of Sarfraz et al. (2013) provides further details of the use of thermal conductivity sensors as IR absorption gas sensors, the entire content of which is incorporated herein by reference.

In another operating mode of the device, the device is operated at the second operating temperature (in one of the ranges for the first operating temperature identified above).

Preferably, the device is operable so that the sensors heat up to the required operating temperature (e.g. a temperature within a range identified above, whether the first operating temperature or the second operating temperature) within a short period of time. This is made more effective by the small thermal mass of the membranes and by the protection of the heater elements against deterioration by being embedded in the membranes. This time is called the response time in this disclosure. Preferably the response time for reaching the required operating temperature from the ambient temperature—the heating response time—is at most 100 ms. More preferably this response time is at most 80 ms, at most 60 ms, at most 40 ms or at most 20 ms. Faster heating response times are possible depending on the sensor design, e.g. down to about 400 µs. Preferably the response time for cooling to ambient temperature (e.g. below 50° C.)—the cooling response time—is slightly longer than the heating response time. Preferably the cooling response time is at most 300 ms. More preferably this response time is at most 200 ms, at most 100 ms, at most 80 ms, at most 50 ms or at most 30 ms. Faster cooling response times are possible depending on the sensor design, e.g. down to about 500 µs. These response times of course depend on the thermal conductivity of the gaseous environment, with a more thermally conductive gaseous environment causing slower heating response times and faster cooling response times. The figures given above are assuming measurement in air at room temperature and pressure.

In the context of a device manufactured using a CMOS processes and/or a SOI process, the metal layer (e.g. tungsten) may be used as an interconnect metal in the CMOS circuitry.

A temperature sensor may be embedded within the membrane and placed below the heater or adjacent to the heater. The temperature sensor may be any of a diode temperature sensor, thermopile temperature sensor, resistive metal temperature sensor and resistive silicon temperature sensor.

A controller circuit for driving the heater, controlling its temperature, signal conditioning and processing of the input signal as well as of the measurands may be fabricated on the same silicon, SOI substrate.

The group of materials from which the heater can be made include aluminium, tungsten, copper, titanium and polysilicon.

The device may be manufactured using MEMS only process.

The heater itself may be used as a temperature sensor.

The device may have four electrical contacts per heater for four-wire sensing.

The device may have a temperature sensor smaller than, larger than or of the same size and dimensions as the heater.

The membrane may be formed by deep reactive ion etching (DRIE), anisotropic wet etching, KOH or TMAH process.

The membrane may be formed on a starting substrate of silicon or SOI wafer.

The device may incorporate an infrared emitter.

The device may incorporate a flow sensor.

The device may incorporate integration of a thermal conductivity sensor and infrared emitter, a temperature sensor and a flow sensor.

The device may be capable of operating in multiple modes integration of a thermal conductivity sensor and infrared emitter, a temperature sensor and a flow sensor.

In another aspect, there is provided an array of thermal conductivity sensors on a chip wherein each thermal conductivity sensor of the array may be as set out above.

The device may incorporate a monocrystalline silicon or a polycrystalline silicon layer used to form a heat spreader plate directly below the resistive heating element.

The device may incorporate a metal layer to form a heat spreader plate adjacent to the heater or above it.

The device may incorporate a protective layer comprising of a layer of silicon oxide or silicon nitride.

The membrane layer may comprise a plurality of stacked silicon oxide layers.

The membrane layer may comprise a plurality of stacked metal layers.

The membrane layer may comprise at least one metal layer to act as etch stop for the recess.

The membrane layer may comprise at least one monocrystalline silicon layer to act as etch stop for the recess.

The group of materials from which the heater can be made includes aluminium, tungsten, copper, titanium, platinum, molybdenum, tantalum, nickel, chromium, gold and polysilicon.

In another aspect, there is provided a method of carrying out thermal conductivity and infrared absorption measurements with a device as set out above.

In another aspect, there is provided a method of carrying out thermal conductivity and flow rate measurements with a device as set out above, In another aspect, there is provided a method of carrying out flow rate and infrared absorption measurements with a device as set out above, In another aspect, there is provided a method of carrying out thermal conductivity, flow rate and infrared absorption measurements with a device as set out above, Further optional features of the invention are set out below.

BRIEF DESCRIPTION OF THE DRAWINGS

Embodiments of the invention will now be described by way of example with reference to the accompanying drawings in which.

Figure 1:
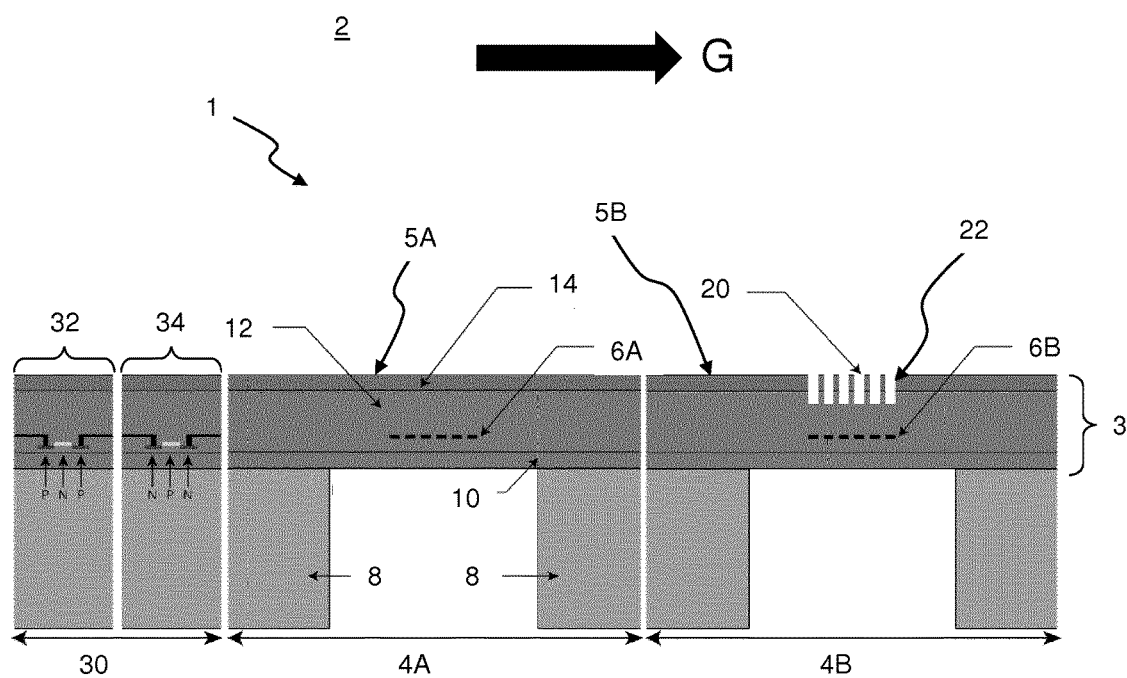
FIG. 1 shows a schematic cross sectional view of an embodiment of the present invention.

DETAILED DESCRIPTION OF THE PREFERRED EMBODIMENTS, AND FURTHER OPTIONAL FEATURES OF THE INVENTION

Before discussing the structure and function of the preferred embodiments of the invention, it is of assistance to consider manufacturing techniques of utility in fabrication devices according to the preferred embodiments.

MEMS based sensors typically translate nonelectrical input signals (picked up by their mechanical micro-structures) into electrical information. These sensors have evolved from the integrated circuit (IC) industry. Silicon micro-machining techniques (primarily surface micro-machining and bulk-micromachining) in combination with standard integrated circuit fabrication processes (including doping, deposition, photolithography, and etching) form the technological base for many MEMS sensors. Such MEMS sensors that are fabricated by using the standard complementary metal oxide semiconductor (CMOS) foundry services are called CMOS MEMS [Brand and Fedder (2008)].

Fabricated CMOS MEMS based sensors involve MEMS specific processing steps at various stages of the fabrication process. They are thus typically classified as:
Pre-CMOS MEMS sensors
Intra-CMOS MEMS sensors
Post-CMOS MEMS sensors Pre-CMOS MEMS Sensors For these sensors the MEMS processing steps are executed before the wafers are sent to the CMOS foundry. Few commercial foundries allow pre-processed wafers to enter their CMOS fabrication process due to stringent manufacturing requirements. These requirements include:
Wafer must have a clean, flat, device-grade silicon surface
Wafers must be free of any contaminants
Wafers must not have any low melting point metals (e.g. aluminium) on them.

Thus the challenge for such sensors involves planarization after MEMS process and interconnection between MEMS and the electronic circuits.

Intra-CMOS MEMS Sensors

These sensors are fabricated using a modular fabrication approach, where MEMS structures (typically made of polysilicon layers) are deposited during a CMOS process flow. After CMOS processing, the MEMS structures are released normally by sacrificial etching of the oxide layer.

Post-CMOS MEMS Sensors

The majority of CMOS MEMS sensors are fabricated using a post CMOS approach to develop the required MEMS structure. This technique facilitates outsourcing of the CMOS electronics development to a CMOS foundry. The MEMS processing can be later executed, on the fully processed CMOS wafers, either at a dedicated MEMS foundry or at the same CMOS foundry provided it offer MEMS processing facilities. These facilities would include but not limited to plasma enhanced chemical vapour deposition (PECVD), sputtering, electroplating, most wet and dry etching techniques and bulk and surface micro-machining processes.

The disadvantage of this approach is that post CMOS processes cannot involve very high temperature processes such as polysilicon low pressure chemical vapour deposition (LPCVD) due to aluminium metallization on CMOS wafers. However, this problem can be circumvented by using special high temperature metallization CMOS process (e.g. tungsten metallization CMOS process is used for the SOI CMOS sensors which constitute the preferred embodiments of the present invention). This option of high temperature metallization CMOS process is also well suited if the sensor application involves either a high temperature environment or if the sensor itself is expected to operate at very high temperatures.

Advantages of CMOS MEMS Sensors

Since CMOS MEMS sensors utilizes industry standard CMOS processes for fabrication of microstructures, by utilizing the metal and inter-metal dielectric layers of the CMOS process, the physical sensor and the sensor drive and signal processing electronics can thus both resides side by side on the same physical chip. Unlike proprietary MEMS processes fabricating CMOS MEMS sensors by utilizing a defined CMOS process benefits from the reliability, capacity, and economies of scale of the global semiconductor market [Brand and Fedder (2008)].

Consequently lower manufacturing costs can be achieved by following the mass production route just like any other CMOS device. In addition to this, having sensor drive, signal conditioning and signal processing electronics residing next to the sensor reduces parasitic signals (arising from transmission line capacitance and inductance) due to the small distance between the two. As the CMOS process is mature and highly repeatable the material properties are tightly controlled thus further reducing parasitic signals compared to discrete MEMS sensors. All these parameters become significantly important and advantageous when the number of sensors on the chip increases. In doing so this approach leads to an overall reduced system size while simultaneously addressing manufacturing costs and reliability issues.

Limitations of CMOS MEMS

CMOS MEMS sensor development has its own set of limitations as well [Brand and Fedder (2008)]. The limitations arise from restricted freedom for the design engineer by following a standardized process. The use of various materials, their dimensions, layout sequence and tolerances are all controlled by the pre-defined CMOS process. This is because the primary aim of the CMOS process is to optimize the electronic circuitry for which it was developed in the first instance. MEMS development never was nor probably will be the primary aim of any CMOS process for the foreseeable future. This is because the market dynamics which dictate the CMOS foundry's commercial interest are primarily CMOS electronics driven.

Another limitation of the CMOS MEMS methodology is the inflexibility of the CMOS foundry towards changes to their fabrication processes. Thus the post CMOS route is the most preferred option as post processing of fully developed CMOS wafers is very much possible and also cost effective.

Design rule checks (DRC) aimed at electronic circuits must also be passed by the MEMS micro structures. Thus any design rule violation can lead to a non-assurance of the sensors' functionality as well overall process yield compromise. Therefore, DRC violations in a CMOS MEMS design have to be carefully scrutinized or waived off.

Thermal Conductivity Sensor Design

A substantial effort to develop MEMS based thermal conductivity sensors has transpired over the last two decades. The reported designs show commercial and technological advances associated with miniaturization of thermal conductivity detectors [US 2013/0256825; WO2011044547; Agilent SI-02239 490 Micro GC Solution Data Sheet. 2010]. This has been possible as thermal conductivity sensors are concentration dependent and not mass dependent. The primary area of application though has remained within the gas chromatography market domain [Sparkman et al. (2011); Sze (1994); Sevcik (1976)].

However, key hurdles in thermal conductivity sensor design still remain. These include limits of detection [Chemical Weapons Convention Chemical Analysis (2005)], cross sensitivity due to their universal behaviour [Mcnair and Miller (2009)], sensor response time and performance degradation due to convective cooling effects [Kaanta et al. (Sensors and Actuators A: Physical, 2011)].

One aim of the inventors' work has been to develop a thermal conductivity sensor which is substantially flow invariant and also preferably flow direction invariant. Another aim has been to develop a sensor using SOI CMOS MEMS technology based on tungsten micro heaters. The choice of using tungsten, used in some SOI CMOS processes as the metallization layer material, over poly-silicon and MOSFETS micro heaters is its ability to operate reliably at higher temperatures [Ali et al. (2008)]. In addition to this, tungsten, unlike aluminium (commonly used as CMOS metallization layer material), does not suffer from electromigration effects and has a melting point of 3410° C. However, it is to be noted that in some embodiments of the invention, aluminium metallization layers are used, for example where the operating temperature (at least in the location of the aluminium metallization) is suitable.

Broadly speaking, the use of SOI technology allows a higher degree of flexibility in the design of thermal conductivity sensors. As an example, an extremely thin (sub 10 µm) membrane can be fabricated along with diode or thermopile based temperature sensors to monitor the resistive heating element's temperature change and account also for flow rate changes. The same wafer can also be used to develop sensor drive and processing electronics capable of withstanding high temperature environments unlike bulk silicon based CMOS electronics. Also the thin membrane provides excellent thermal isolation between the sensor and processing electronics as demonstrated by I. Haneef (2009) for SOI CMOS MEMS flow sensors.

Figure 8:
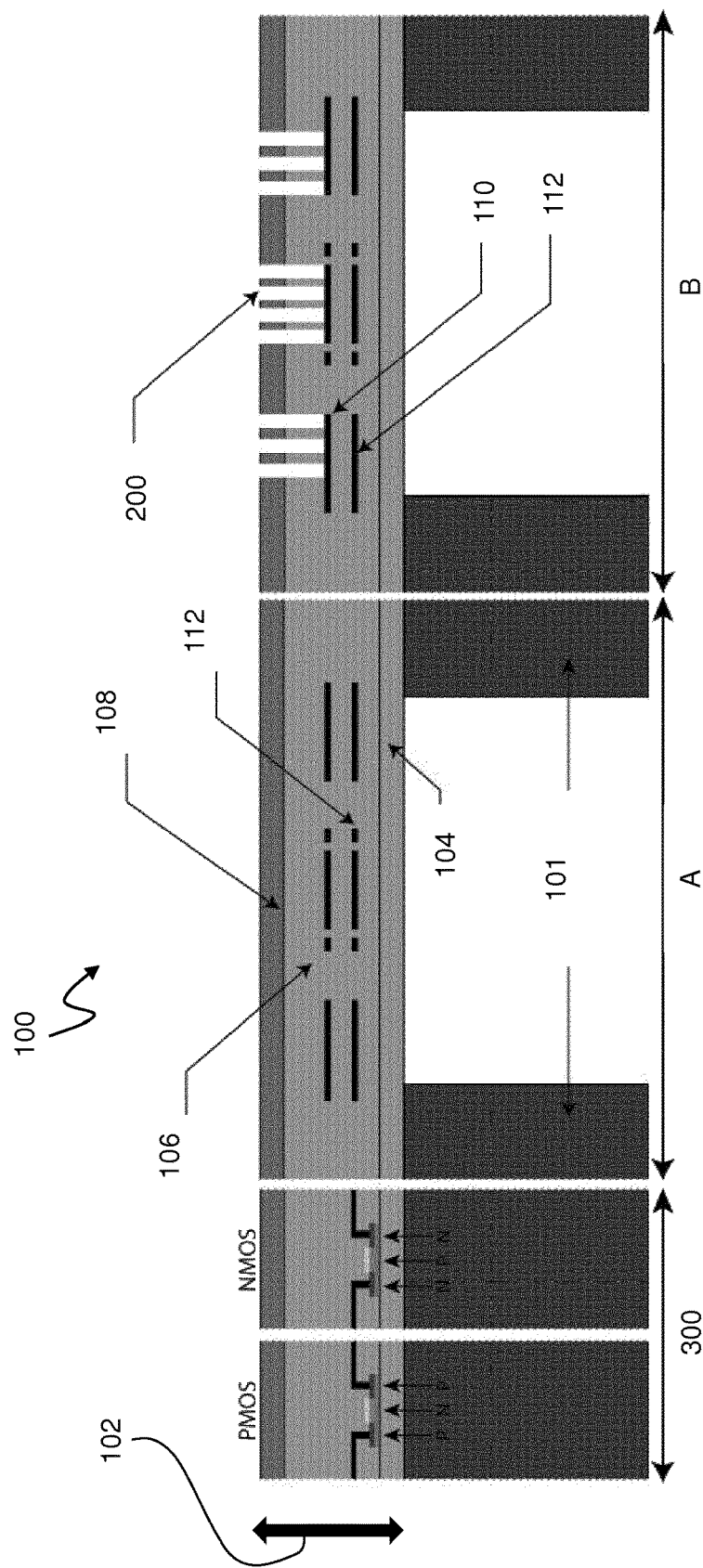
FIG. 8 shows a schematic cross sectional view of another embodiment of the present invention.

A simplified proposed flow invariant thermal conductivity sensor using SOI CMOS MEMS technology is shown in FIG. 1, which is described in more detail below. The metal layers, used as interconnects for CMOS circuitry, are used to form the tungsten micro heaters along with the vertical grooves. A post CMOS Deep Reactive Ion Etch (DRIE) step is then carried out to achieve a thin membrane. Constructional details of a preferred modified proposed flow invariant thermal conductivity sensor is shown in FIG. 8 and described in more detail below.

Structure and Function of the Preferred Embodiments

Thermal conductivity sensors make use of heat transfer effects as a result of changes in thermal conductivity with gas composition. Such thermal effect measurement of gases is an established sensing technique to accurately measure gas concentrations. It has been considered to be most effective under low convective flows and for gases with large differences in molecular weight such as hydrogen in air. For gases with close thermal conductivity values measured in forced convective environments it is necessary to develop highly sensitive and flow invariant thermal conductivity sensors.

FIG. 1 shows a schematic simplified cross sectional view of an embodiment of the present invention. Thermal conductivity sensing device 1 is made up of two sensors 4A and 4B, and an electronics portion 30. The device 1 is configured to lie in the flowpath of a gas G, close to an outlet of a gas chromatography system (not shown), for example. Alternatively the device can be located inside a column (or micro-column) or be part of the column (or micro-column). The gas is configured to flow in flowpath G and flows over the sensors 4A, 4B through channel 2. In the device 1 shown in FIG. 1, sensors 4A and 4B are substantially identical, differing only in the presence of a flow altering means 20 on sensor 4B. This will be described in more detail below.

The structure of sensor 4B will now be described with reference to schematic FIG. 1. Sensor 4A differs only in the absence of flow altering means 20, and so will not be described separately in order to avoid unnecessary repetition.

Sensor 4B includes a series of layers. The membrane stack 3 of the sensor 4B is mounted on a silicon substrate 8. The membrane stack 3 of the sensor 4B is made up of several layers in this simplified embodiment. The membrane stack 3 includes silicon dioxide layers 10, 12, metal heater layer 6B and a top silicon nitride passivation layer 14. These membrane stacks are produced by performing a Deep Reactive Ion Etch step on the back side of a SOI wafer, as a post-CMOS processing step, in order to selectively remove the silicon substrate in the area corresponding to the membrane.

The silicon substrate 8 which supports the membrane stack provides the necessary robust mechanical structure and an area for developing sensor interface and processing electronics. The substrate 8 also acts as a heat sink, in order to maintain the edge of the membrane at constant ambient environment temperature. Tungsten micro-heater 6B is embedded inside the silicon dioxide layer 12 of the membrane stack. The tungsten micro heater 6B is a resistive heating element, and the power lost by this micro-heater 6B is a representation of the heat lost, in part, to the gas in gas flowpath G.

In a stationary gaseous environment, the rate at which heat flows from the heated element 6B to the walls of the channel 2 is a function of the thermal conductivity of the fluids inside the channel 2. However, in a flowing gaseous environment, the heat lost to the gas in the flowpath G has contributions from thermal conduction, but also from forced convection. The contribution from forced convection arises as a result of the bulk movement of the gas carrying heat away. The contribution from thermal conduction arises as a result of conduction of heat through the gas across the channel 2. There may be other contributions to the heat loss. IR radiation, however, is negligible at low operating temperatures. At high operating temperatures, IR radiation is non-negligible, allowing to be used to investigate both infrared absorption and thermal conductivity. In a forced convective environment there is considered to be no natural convection above the membrane. Below the membrane there is typically natural convection unless the cavity area is also exposed to gas flow.

The silicon nitride passivation layer 14 protects the sensor 4B from environmental damage such as corrosion and undesirable oxidation. The upper surface 5B of the passivation layer acts as a surface for thermal contact between the sensor 4B and the gas in flowpath G.

Tungsten micro-heater 6B is embedded inside silicon dioxide layer 12 directly beneath flow altering means 20 (or in alternative embodiments, surrounding the flow altering means). In this embodiment, flow altering means 20 takes the form of a series of parallel vertical grooves 22. Six grooves are shown for the sake of simplicity and ease of illustration. These grooves have a substantially rectangular profile as shown in FIG. 1 and are deeper than they are wide.

CMOS electronics 30 are made up of two sections, PMOS section 32 and NMOS section 34, of standard design.

In the embodiment of FIG. 1, sensor 4B, sensor 4A and the CMOS electronics 30 are situated in the gas flowpath G, with the gas flowing in a channel 2 above and over the device, and optionally also beneath it. It will be understood that the orientation of the device is not critical; the device shown in FIG. 1 can be inverted, for example, and yet still operate satisfactorily provided that the sensors are exposed to the gaseous environment. In operation, as gas flows over the device 1, gas molecules are trapped in the grooves 22 of sensor 4B. Because of the geometry of the grooves 22, the molecules which enter the grooves 22 are subsequently substantially unaffected by the flow of the gas G, and are either substantially stationary, or moving in vortices which are substantially permanently confined to the groove 22. The transfer of heat as a result of forced convention (discussed in more detail in the "Experimental Results" section) in the regions of channel 2 which are situated above sensors 4A and 4B respectively, are substantially identical. The contribution, from forced convection alone, to the power loss recorded in each of the tungsten micro-heaters 6A and 6B, is therefore also substantially equal.

Furthermore, the membrane stack 3 of sensor 4B therefore has a slightly different thermal conductivity from the membrane stack 3 of sensor 4A, as a consequence of the presence of gas molecules being trapped within the grooves 22, (the gas having a different thermal conductivity from the materials from which the membrane stack 3 is made). Therefore, the contribution to the power loss in tungsten micro-heaters 6A and 6B which arises as a result of heat loss due to lateral thermal conduction in the membrane, is different in each of micro-heaters 6A and 6B.

Therefore, a differential measurement between sensors 4A and 4B substantially cancels out the contribution of heat loss due to forced convection, and provides a reading due to the resulting differing thermal conductivity of each of the membrane stacks 3. From a signal representative of this, the thermal conductivity of the gas in flowpath G can be deduced. Changes in this thermal conductivity can therefore be used to sense the presence of different gases in the channel 2.

The fluid under test (sample fluid) and the carrier fluid will have different thermal conductivity values (such as 1% hydrogen in argon). Furthermore, the heat transfer properties of the sample fluid mixed with the carrier fluid varies with the concentration of the sample fluid in the carrier fluid. Changes in thermal conductivity are then typically measured as voltage changes but can also be directly interpreted by the micro heater's resistance or power consumption changes.

Two different operating approaches can be used to determine the thermal conductivity of the fluid. In constant voltage or constant current approach, the output of the sensor is related to the temperature change of the heating element. As a less thermally active fluid is exposed to the detector, less heat is transported away, increasing the heating element temperature. The opposite would apply in case of high thermally active fluids. In a constant temperature approach, the heating element is maintained at a predetermined temperature. The change in power required to maintain this predetermined temperature is measured. The first approach is used in the discussion below to measure sensor response to various gases.

FIG. 8 shows a schematic cross sectional view of a preferred embodiment of the present invention. Thermal conductivity sensing device 100 is made up of two CMOS sensors A and B, and a CMOS electronics portion 300. The device 100 is configured to lie in the flowpath of a gas as for the embodiment of FIG. 1. In the device 100, sensors A and B are substantially identical, differing only in the presence of a flow altering means 200 on sensor B. This are described in more detail below. The device is formed using a silicon substrate 101 (SOI wafer).

Sensor B includes a series of layers. The membrane stack 102 of the sensor B is made up of several layers. The membrane stack is the buried oxide layer of the SOI wafer structure plus active silicon and polysilicon layers on top followed by multiple metallization layers with inter layer dielectric medium (typically silicon dioxide) as separator. In terms of the features seen in FIG. 8, the membrane stack 102 is composed of layers of silicon dioxide 104, 106, thin films of metal (described further below) and a top silicon nitride (or a mix of silicon nitride and silicon dioxide) passivation layer 108. These membrane stacks are produced by performing a Deep Reactive Ion Etch step on the back side of a SOI wafer, as a post-CMOS processing step, in order to selectively remove the silicon substrate in the area corresponding to the membrane.

The membrane stack may include one, two, three or more metallization layers, dependent on the fabrication process. Thus a different CMOS process may have 4 metal layers or even 6 or 10 metal layers.

In FIG. 8, metallization layer 110 is formed of tungsten. Metallization layer 112 is also formed of tungsten and operates as a heater element. An identical heater 112 is formed in sensor A. It will be understood that different metallization layers, in other embodiments, may be formed of different compositions.

Figure 9:
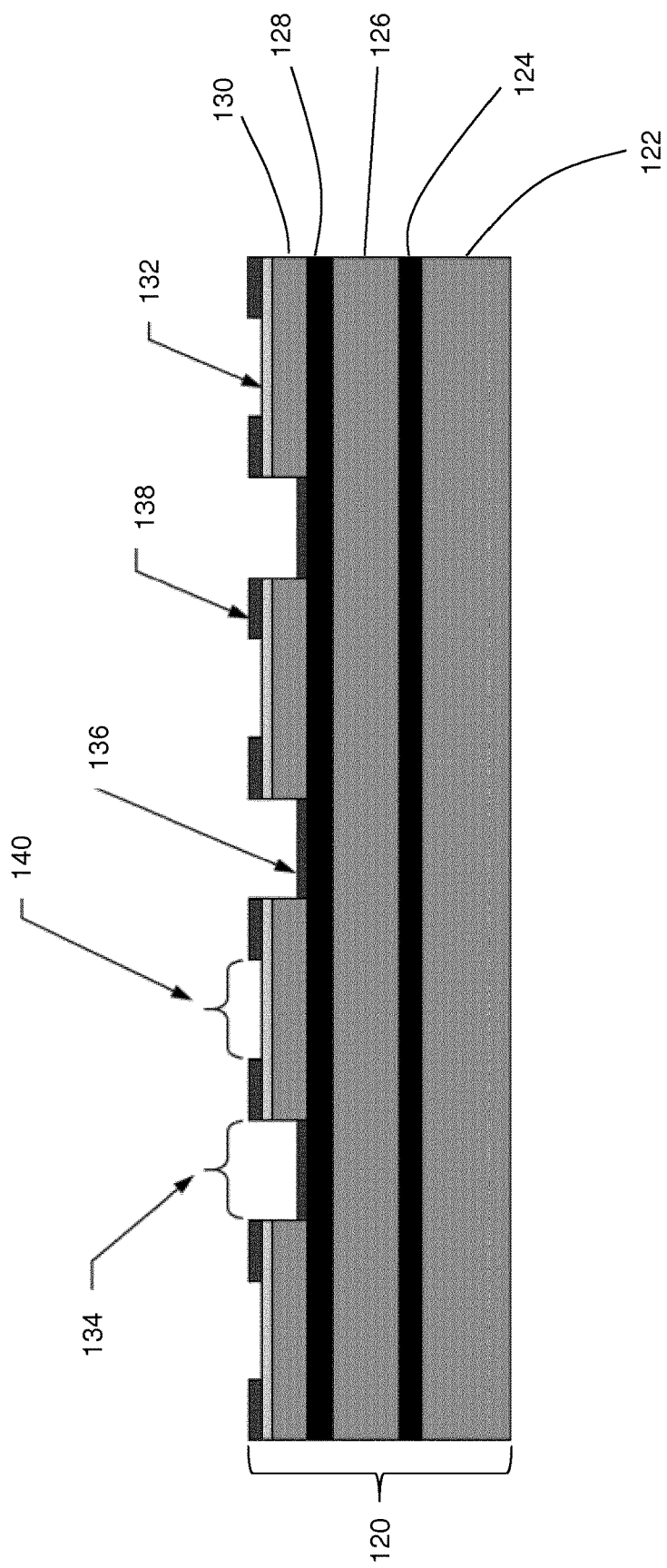
FIG. 9 shows a schematic cross sectional view of a membrane structure for use in an embodiment of the invention.

FIG. 9 shows a schematic cross sectional view of a membrane structure 120 suitable for use in an embodiment of the invention. The membrane structure is formed starting from a stacked arrangement of first silicon dioxide layer 122, first tungsten metallization layer 124, second silicon dioxide layer 126, second tungsten metallization layer 128, third silicon dioxide layer 130 and passivation layer 132. Major recess 134 is etched into the membrane structure, ending at second tungsten metallization layer 128. An aluminium metallization layer 136 is formed at the base of the major recesses and an aluminium metallization layer 138 over the passivation layer 132. As will be understood, layers 136, 138 may be formed in the same step. Aluminium metallization layer 138 is patterned to form minor recesses 140.

Figure 2:
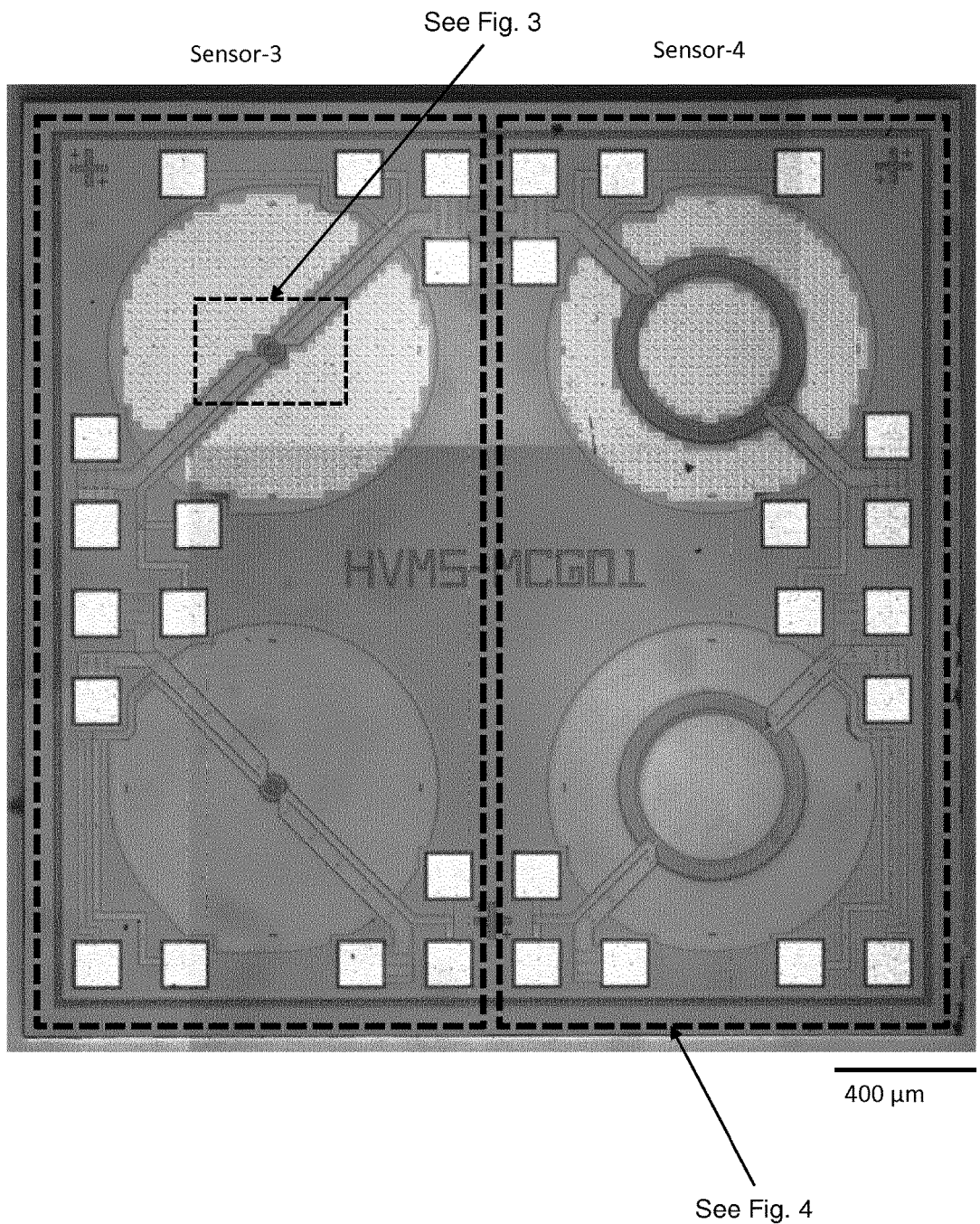
FIG. 2 shows an optical microscope plan view image of a fabricated device of an embodiment of the present invention, incorporating areas designated "Sensor-3" and "Sensor-4".
Figure 3:
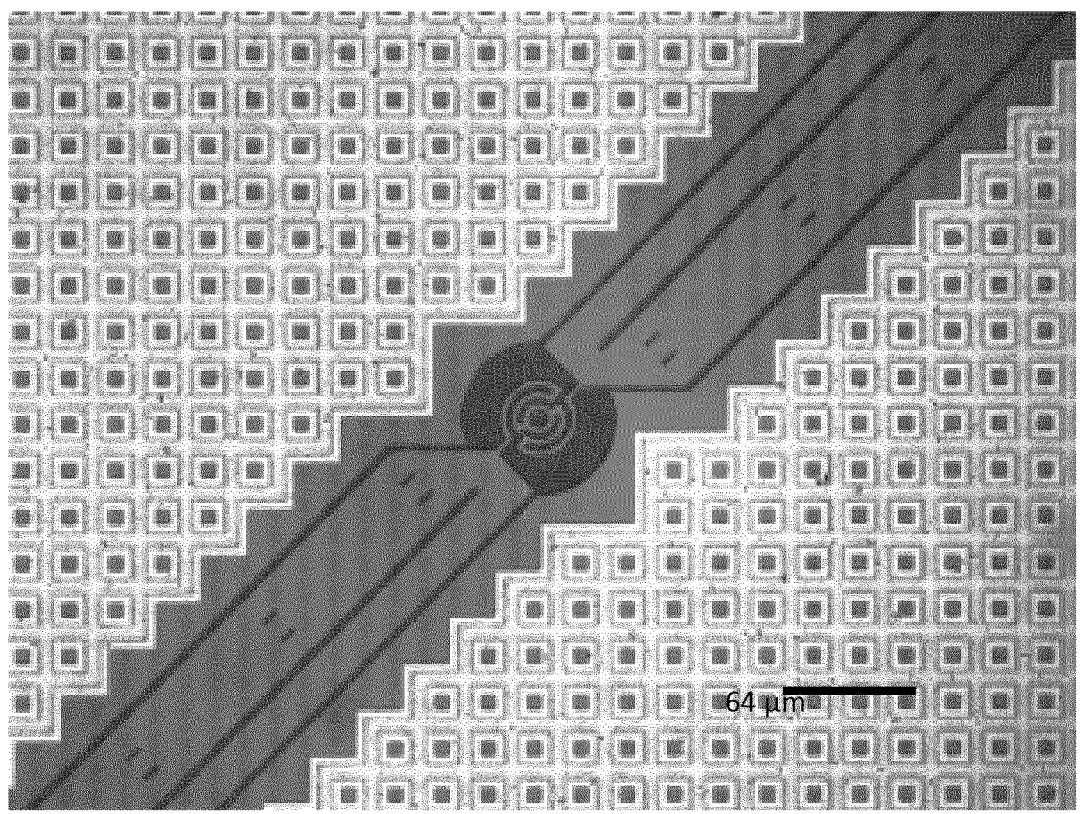
FIG. 3 shows an enlarged view of an area of Sensor-3 of FIG. 2, indicated with a dashed line box.
Figure 4:
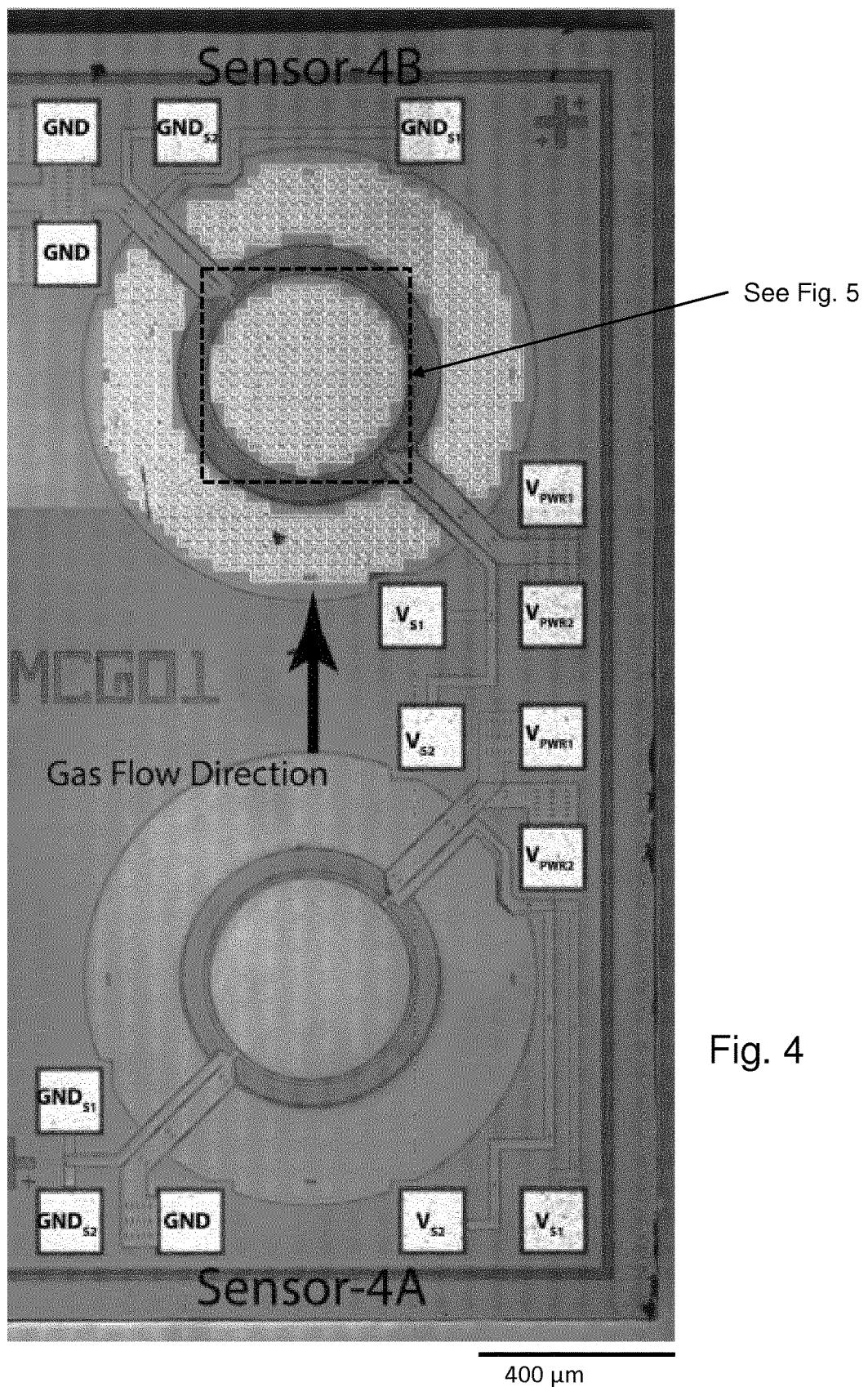
FIG. 4 shows an enlarged view of Sensor-4 of FIG. 2, in which the lower sensor is designated "Sensor-4A" and the upper sensor is designated "Sensor-4B".
Figure 5:
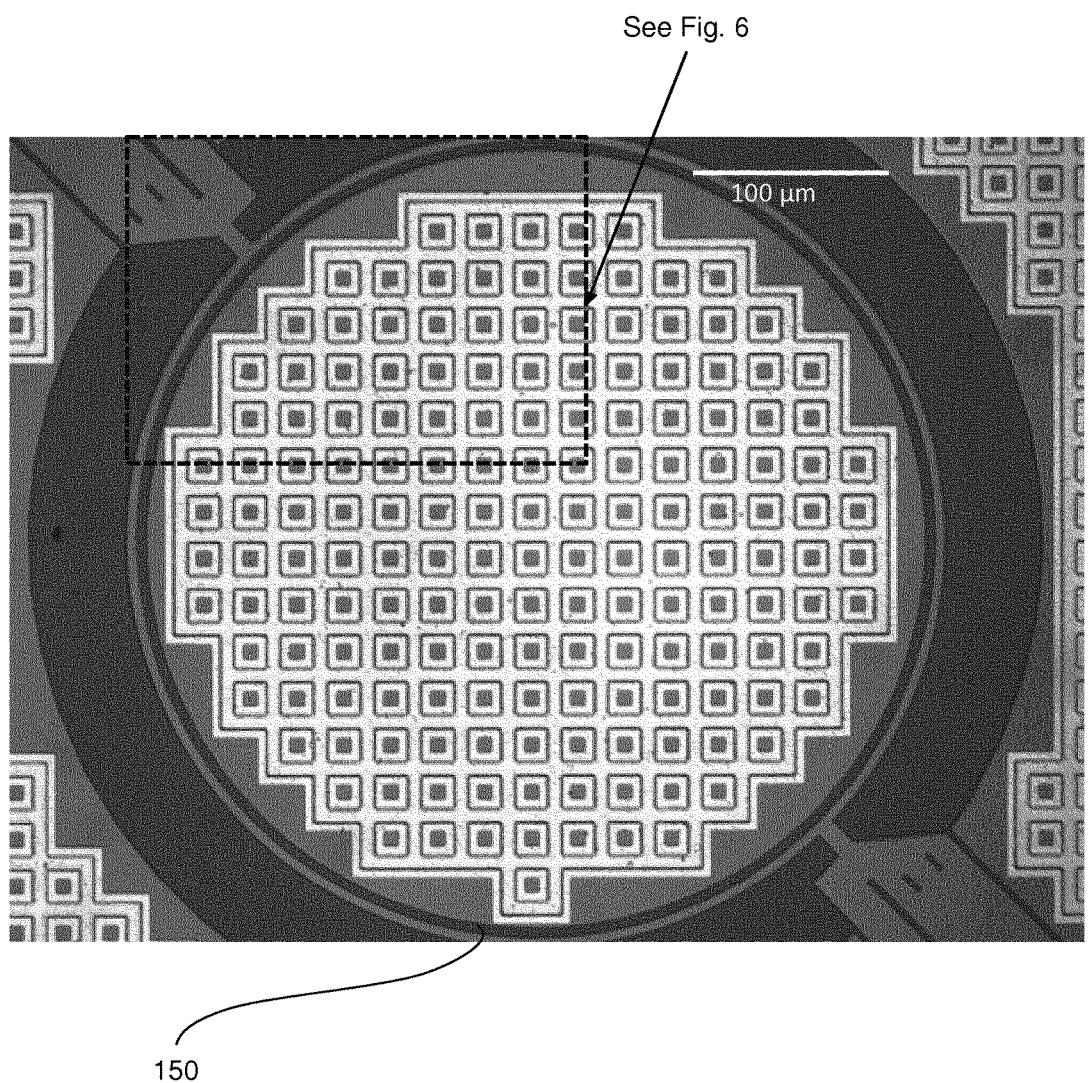
FIG. 5 shows an enlarged view of an area of Sensor-4B of FIG. 4, indicated with a dashed line box.
Figure 6:
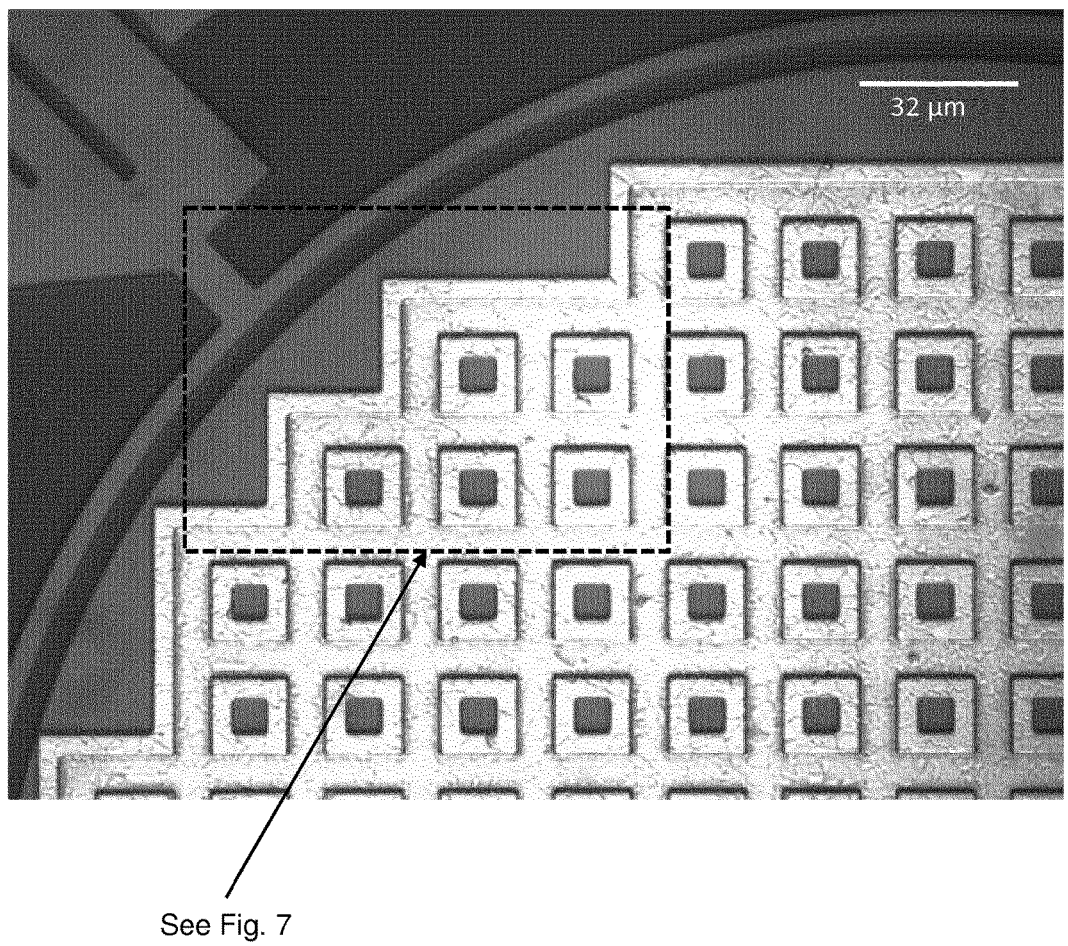
FIG. 6 shows an enlarged view of an area of Sensor-4B of FIG. 5, indicated with a dashed line box.
Figure 7:
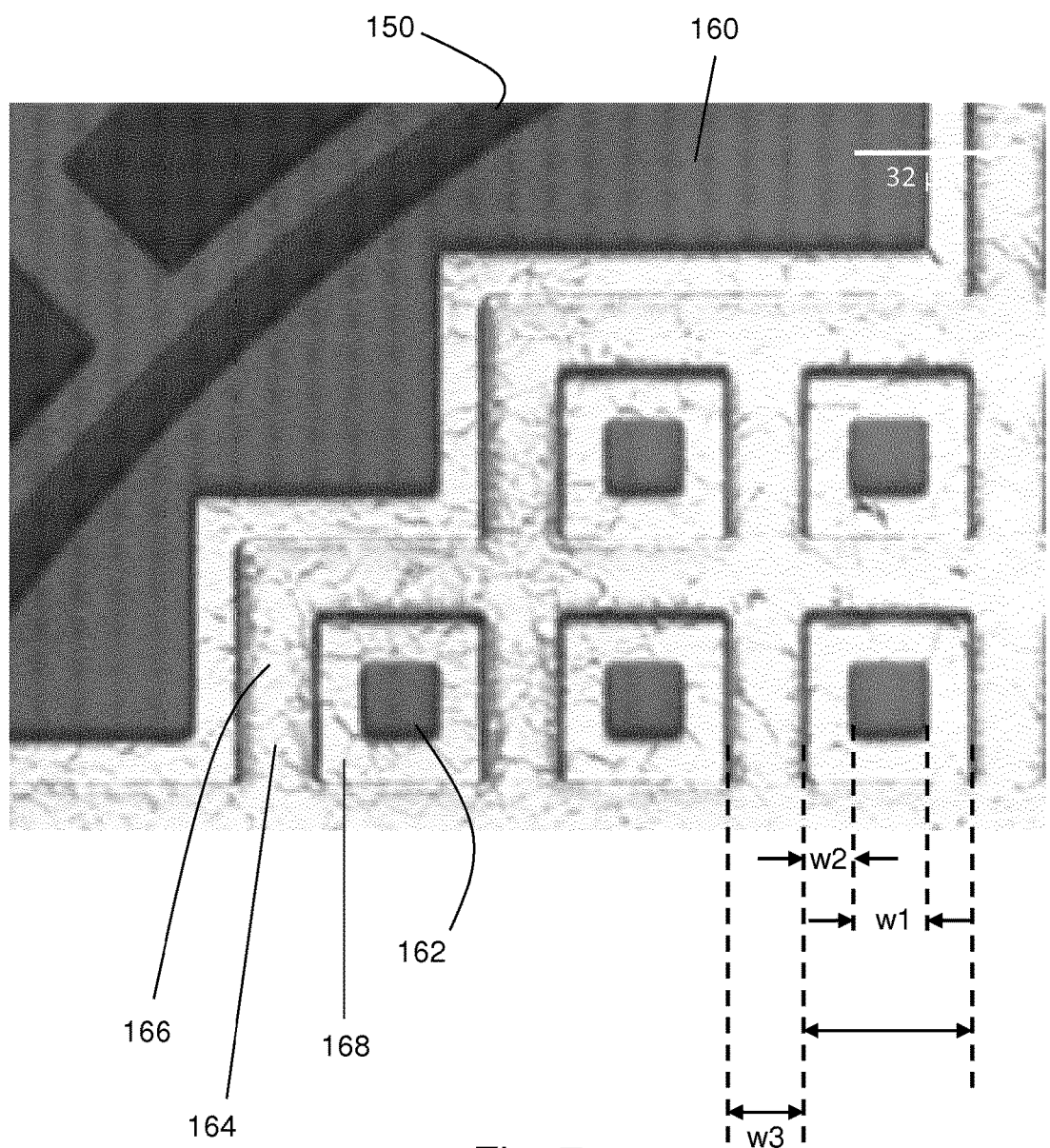
FIG. 7 shows an enlarged view of an area of Sensor-4B of FIG. 6, indicated with a dashed line box.

FIG. 2 shows an optical microscope plan view image of a fabricated device of an embodiment of the present invention, incorporating areas designated "Sensor-3" and "Sensor-4". FIG. 3 shows an enlarged view of an area of Sensor-3 of FIG. 2, indicated with a dashed line box. FIG. 4 shows an enlarged view of Sensor-4 of FIG. 2, in which the lower sensor is designated "Sensor-4A" and the upper sensor is designated "Sensor-4B". FIG. 5 shows an enlarged view of an area of Sensor-4B of FIG. 4, indicated with a dashed line box. FIG. 6 shows an enlarged view of an area of Sensor-4B of FIG. 5, indicated with a dashed line box. FIG. 7 shows an enlarged view of an area of Sensor-4B of FIG. 6, indicated with a dashed line box. The structure of the flow altering means for Sensor-4B is intended to be the same as illustrated schematically in FIG. 9.

Sensor-3A and Sensor-3B are identical except for an arrangement of flow altering means at the surface of the membrane of Sensor-3B. The membranes for these sensors are circular in plan view. The heater is located inwardly of the flow altering means.

Sensor-4A and Sensor-4B are identical except for an arrangement of flow altering means at the surface of the membrane of Sensor-4B. The flow altering means have a similar structure, individually, to the flow altering means used for Sensor-3B. The heater 150 in this embodiment is most clearly shown in FIG. 5, as a thin circular shape surrounding the innermost flow altering means.

Referring now to FIG. 7, the structure of the flow altering means is explained. Passivation layer 160 is shown around the flow altering means and at the base of minor recess 162. Aluminium layer 164 is shown at the base of major recess 166 and overlying the passivation layer interposed as a ridge 168 between the major recess 166 and the minor recess 162.

The major recesses 166 therefore form an arrangement of rectilinear grooves, intersecting at right angles. The minor recesses 162 form an arrangement of square holes. The flow altering means in this construction is found to be advantageous in terms of its lack of sensitivity to the direction of gas flow. This is considered to be a flow direction invariant arrangement.

Figure 10:
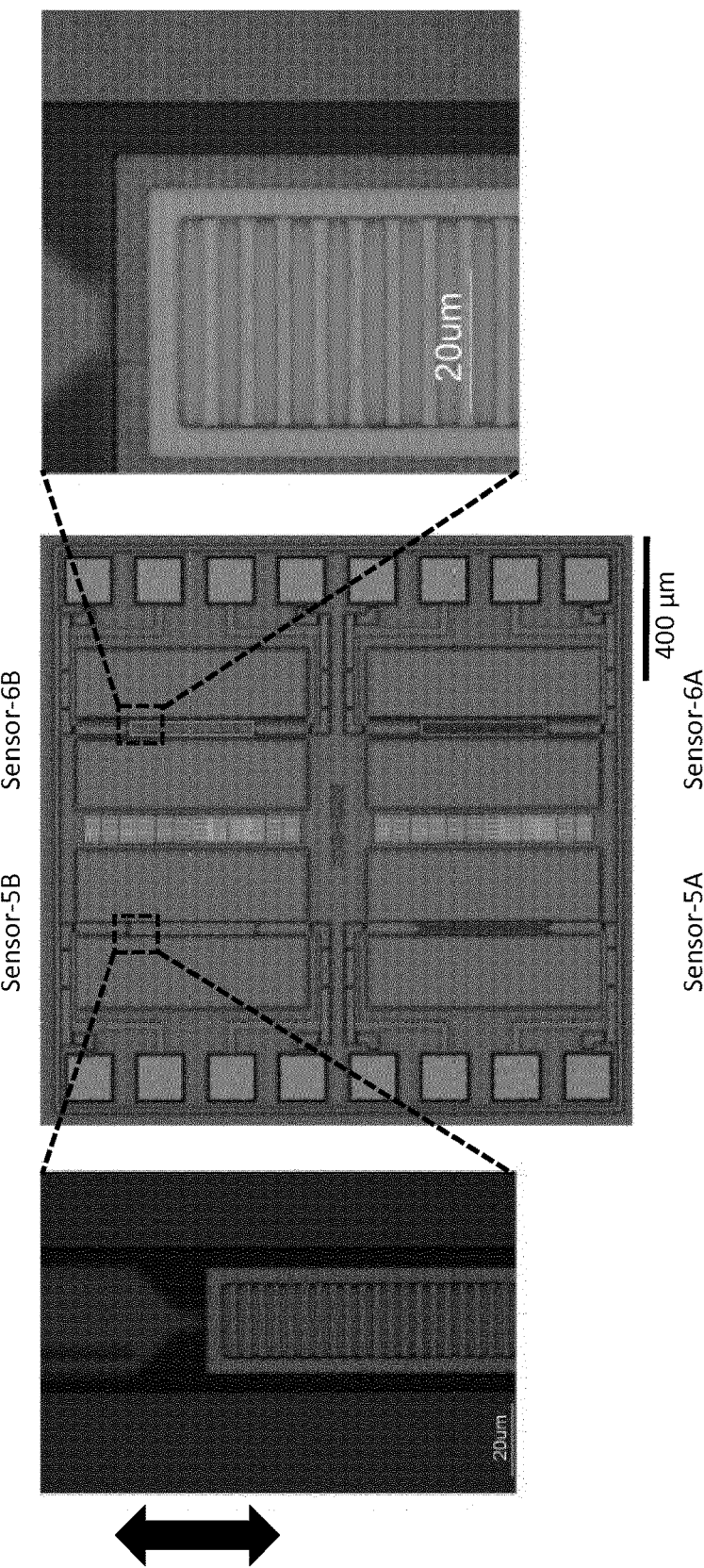
FIG. 10 shows an optical microscope plan view image of a fabricated device of an embodiment of the present invention, incorporating areas designated "Sensor-5A", "Sensor-5B", "Sensor-6A", and "Sensor-6B". The insets show enlarged views of part of Sensor-5B and Sensor-6B respectively.

FIG. 7 indicates certain width dimensions for different features of the flow altering means:
The width w1 of minor recess 162 is about 8 μm.
The width w2 of ridge 168 is about 4 μm.
The width w3 of major recess 164 is about 8 μm.
For the fabricated devices Sensor 3 and Sensor 4:
Depth of the minor groove is around 0.5 μm
Depth of major groove is around 1.35 μm FIG. 10 shows an optical microscope plan view image of a fabricated device of another embodiment of the present invention, incorporating areas designated "Sensor-5A", "Sensor-5B", "Sensor-6A", and "Sensor-6B". The insets show enlarged views of part of Sensor-5B and Sensor-6B respectively. Sensor-5A and Sensor-5B are identical apart from that Sensor-5B has flow altering means in the form of grooves. These are aligned perpendicular to the gas flow direction, indicated by double headed arrow in FIG. 10. In Sensor-5B, the heater is located embedded in the membrane beneath the flow altering means. Sensor-6A and Sensor-6B are identical apart from that Sensor-6B has flow altering means in the form of grooves. In Sensor-6B, the heater is located embedded in the membrane to surround the flow altering means. The grooves of the flow altering means of Sensor-6B are deeper and slightly wider than the grooves of the flow altering means of Sensor-5B.

Figure 11:
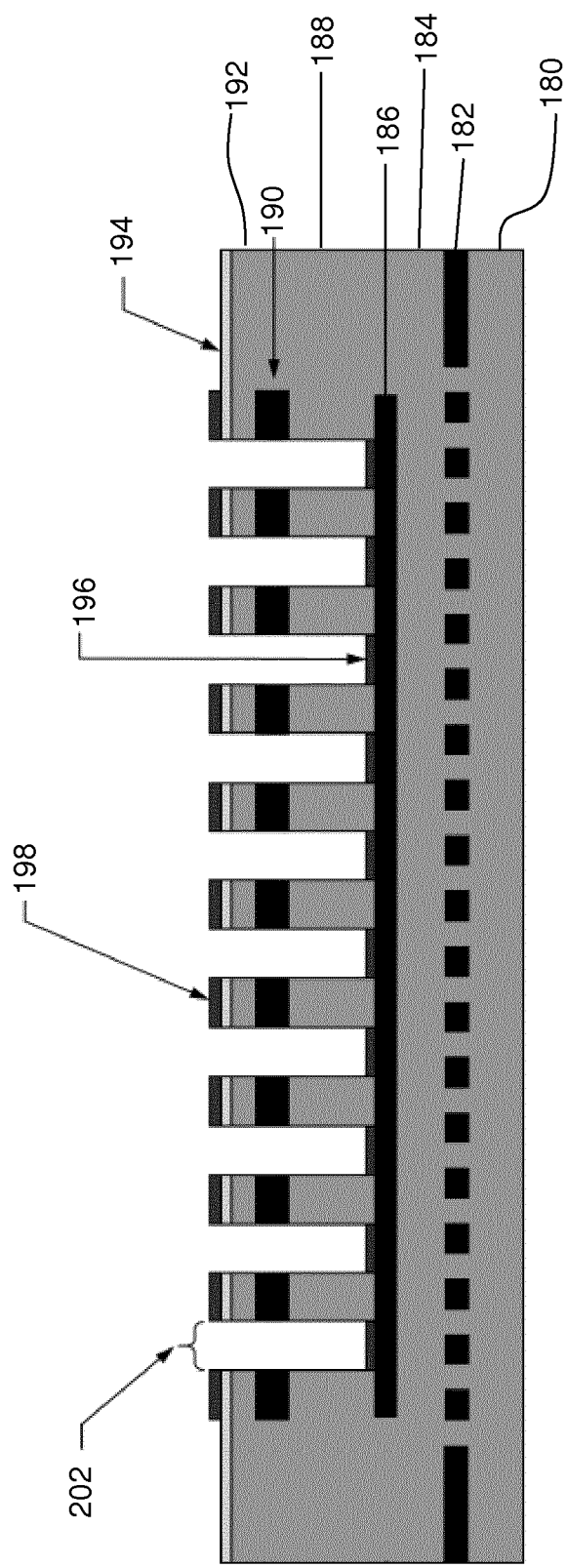
FIG. 11 shows a schematic cross sectional view of the membrane structure of Sensor-5B of FIG. 10, the cross sectional view being taken in the gas flow direction along the centre line of the sensor.

FIG. 11 shows a schematic cross sectional view of the membrane structure of Sensor-5B of FIG. 10, the cross sectional view being taken in the gas flow direction along the centre line of the sensor. The membrane is built up as a stack of layers, incorporating silicon dioxide layer 180, tungsten metal heater 182, silicon dioxide layer 184, tungsten metal layer 186, silicon dioxide layer 188, tungsten metal layer 190, silicon dioxide layer 192 and passivation layer 194. Grooves 202 are formed through the membrane down to tungsten metal layer 186. Aluminium layer 196 is formed at the base of the grooves and aluminium layer 198 is formed on top of the remaining passivation layer 194 between the grooves.

Figure 12:
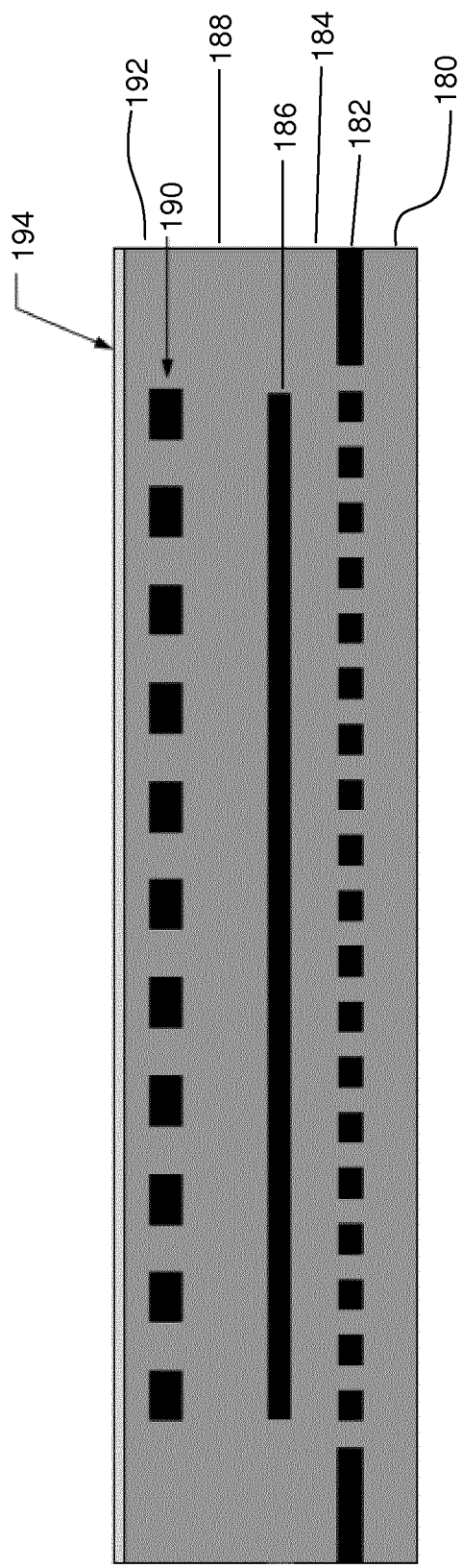
FIG. 12 shows a schematic cross sectional view of the membrane structure of Sensor-5A of FIG. 10, the cross sectional view being taken in the gas flow direction along the centre line of the sensor.

FIG. 12 shows a schematic cross sectional view of the membrane structure of Sensor-5A of FIG. 10, the cross sectional view being taken in the gas flow direction along the centre line of the sensor. The structure is the same as for Sensor-5B, except that grooves are not present, and so the same reference numbers are used in FIG. 12 as in FIG. 11.

Figure 13:
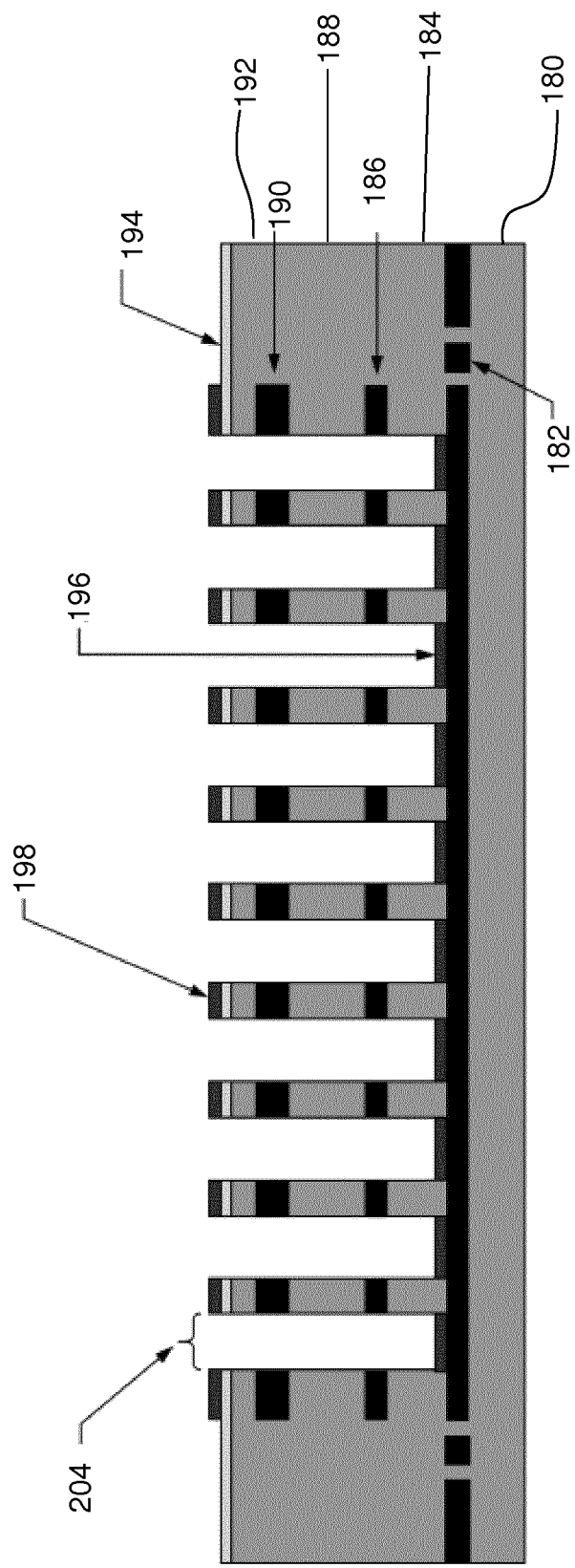
FIG. 13 shows a schematic cross sectional view of the membrane structure of Sensor-6B of FIG. 10, the cross sectional view being taken in the gas flow direction along the centre line of the sensor.

FIG. 13 shows a schematic cross sectional view of the membrane structure of Sensor-6B of FIG. 10, the cross sectional view being taken in the gas flow direction along the centre line of the sensor. The membrane is built up as a stack of layers, incorporating silicon dioxide layer 180, tungsten metal heater 182, silicon dioxide layer 184, tungsten metal layer 186, silicon dioxide layer 188, tungsten metal layer 190, silicon dioxide layer 192 and passivation layer 194. Grooves 204 are formed through the membrane down to tungsten metal heater 182. Aluminium layer 196 is formed at the base of the grooves and aluminium layer 198 is formed on top of the remaining passivation layer 194 between the grooves.

Figure 14:
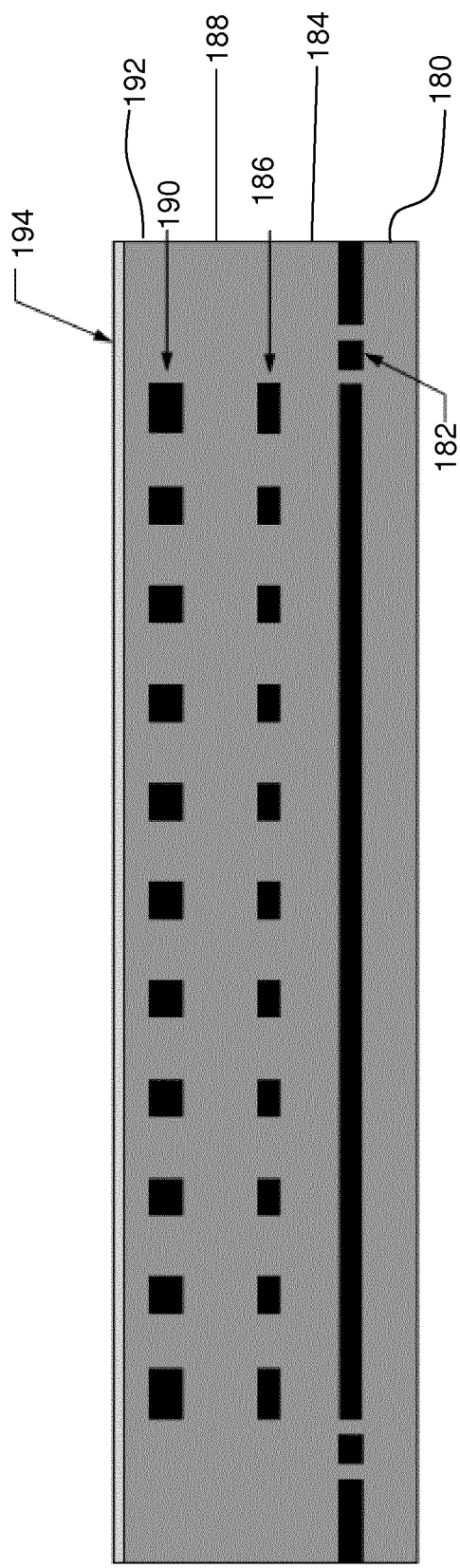
FIG. 14 shows a schematic cross sectional view of the membrane structure of Sensor-6A of FIG. 10, the cross sectional view being taken in the gas flow direction along the centre line of the sensor.

FIG. 14 shows a schematic cross sectional view of the membrane structure of Sensor-6A of FIG. 10, the cross sectional view being taken in the gas flow direction along the centre line of the sensor. The structure is the same as for Sensor-6B, except that grooves are not present, and so the same reference numbers are used in FIG. 14 as in FIG. 13.

Figure 15:
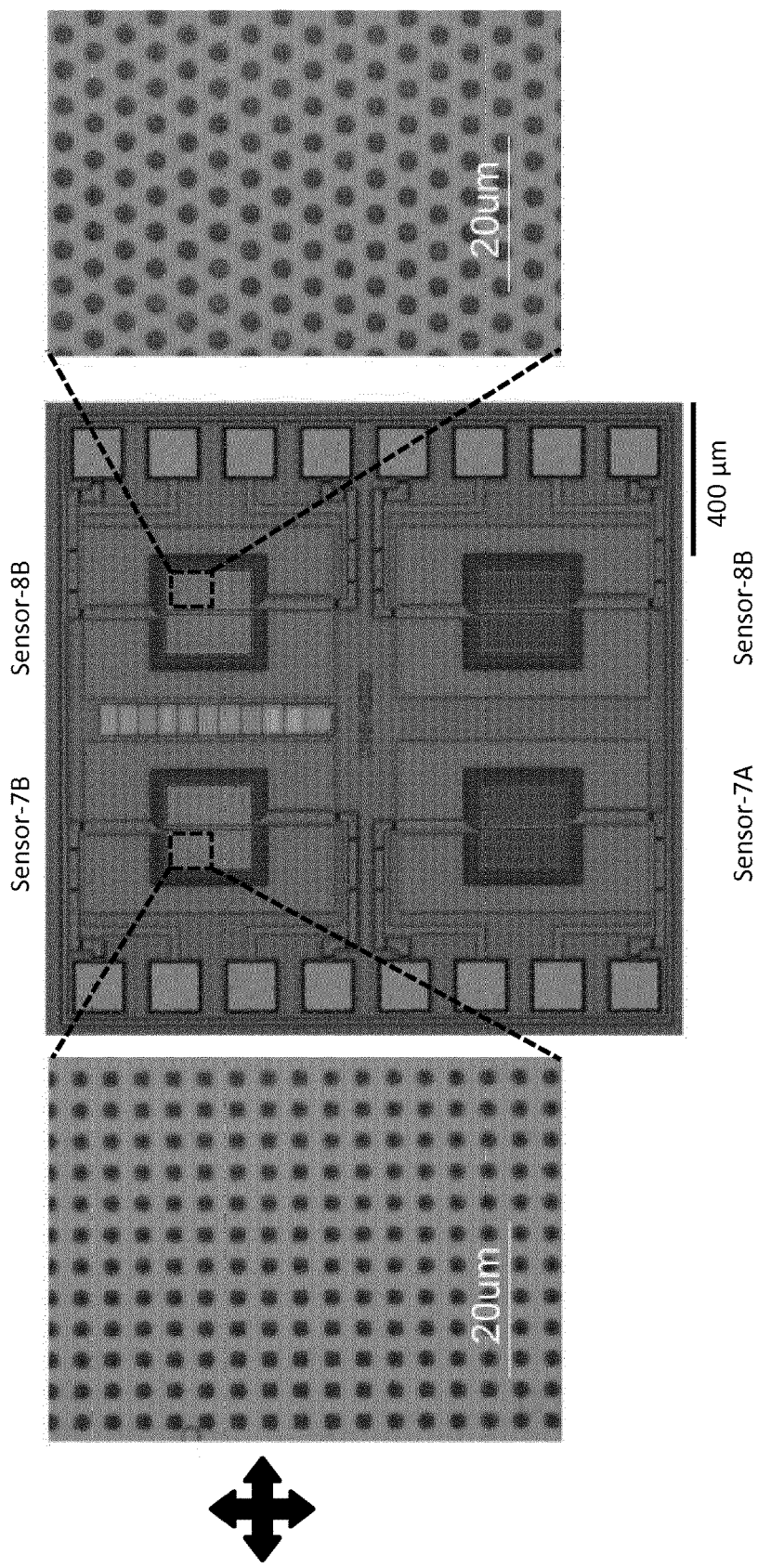
FIG. 15 shows an optical microscope plan view image of a fabricated device of an embodiment of the present invention, incorporating areas designated "Sensor-7A", "Sensor-7B", "Sensor-8A", and "Sensor-8B". The insets show enlarged views of part of Sensor-7B and Sensor-8B respectively.

For Sensor 5:

Depth of groove is approximately 2.34 μm for Al metal layer and 1.9 μm for W metal layer For Sensor 6:

Depth of groove is approximately 2.85 μm for Al metal layer and 3.64 μm for W metal layer FIG. 15 shows an optical microscope plan view image of a fabricated device of an embodiment of the present invention, incorporating areas designated "Sensor-7A", "Sensor-7B", "Sensor-8A", and "Sensor-8B". The insets show enlarged views of part of Sensor-7B and Sensor-8B respectively. In this embodiment, the flow altering means comprises arrays of recesses in the form of equi-axed holes. This provides the device with flow direction invariant operation, as indicated by the multi-headed arrow in FIG. 15.

For Sensor 7 and 8:

Depth of groove is approximately 2.85 μm for Al metal layer and 3.64 μm for W metal layer Other suitable embodiments have groove depth up to 20 μm for a maximum membrane thickness of 25 μm, subject to design of the sensor.

It should be noted that although the devices described are formed with tungsten metal layers, it is possible also to form the devices using aluminium metal layers.

Figure 16:
FIGS. 16-28 show schematic cross sectional views indicating different recess (e.g. groove or hole) shapes for use in embodiments of the present invention.
Figure 17:
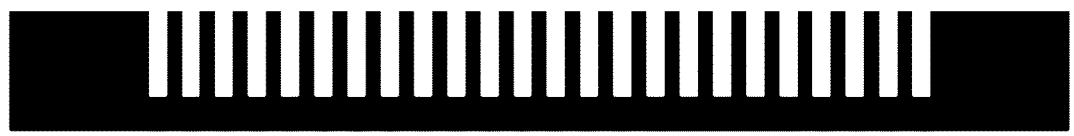
Figure 18:
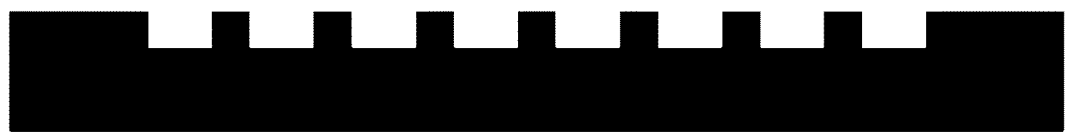
Figure 19:
Figure 20:
Figure 21:
Figure 22:
Figure 23:
Figure 24:
Figure 25:
Figure 26:
Figure 27:
Figure 28:
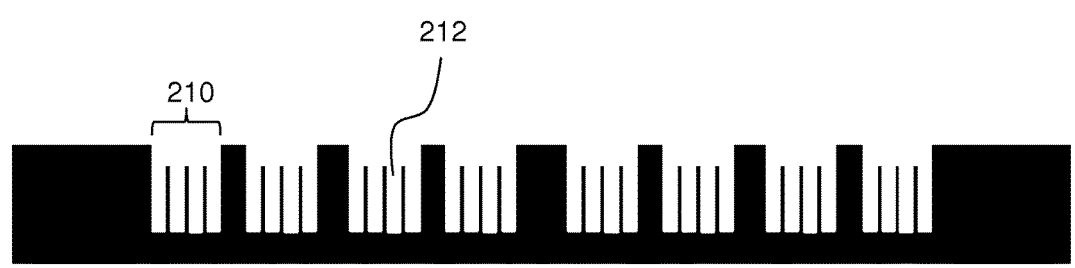

FIGS. 16-28 show schematic cross sectional views indicating different recess (e.g. groove or hole) shapes for use in embodiments of the present invention. The recesses in FIGS. 16 and 17 are similar except for a difference in depth. The recesses in FIGS. 18 and 19 are wider than in FIGS. 17 and 18. The recesses in FIGS. 20 and 21 have a trapezoidal cross sectional shape in contrast to the rectangular cross sectional shape in FIGS. 16 to 19. The shape is narrower at the top than at the base. The recesses in FIGS. 22 and 23 are wider than in FIGS. 20 and 21. The recesses in FIGS. 24 and 25 also have a trapezoidal cross sectional shape but the shape is wider at the top than at the base. The recesses in FIGS. 26 and 27 are wider than in FIGS. 24 and 25. The structure shown in FIG. 28 is of a complex form, having a major recess 210 and minor recesses 212 formed within the major recess.

Figure 29:
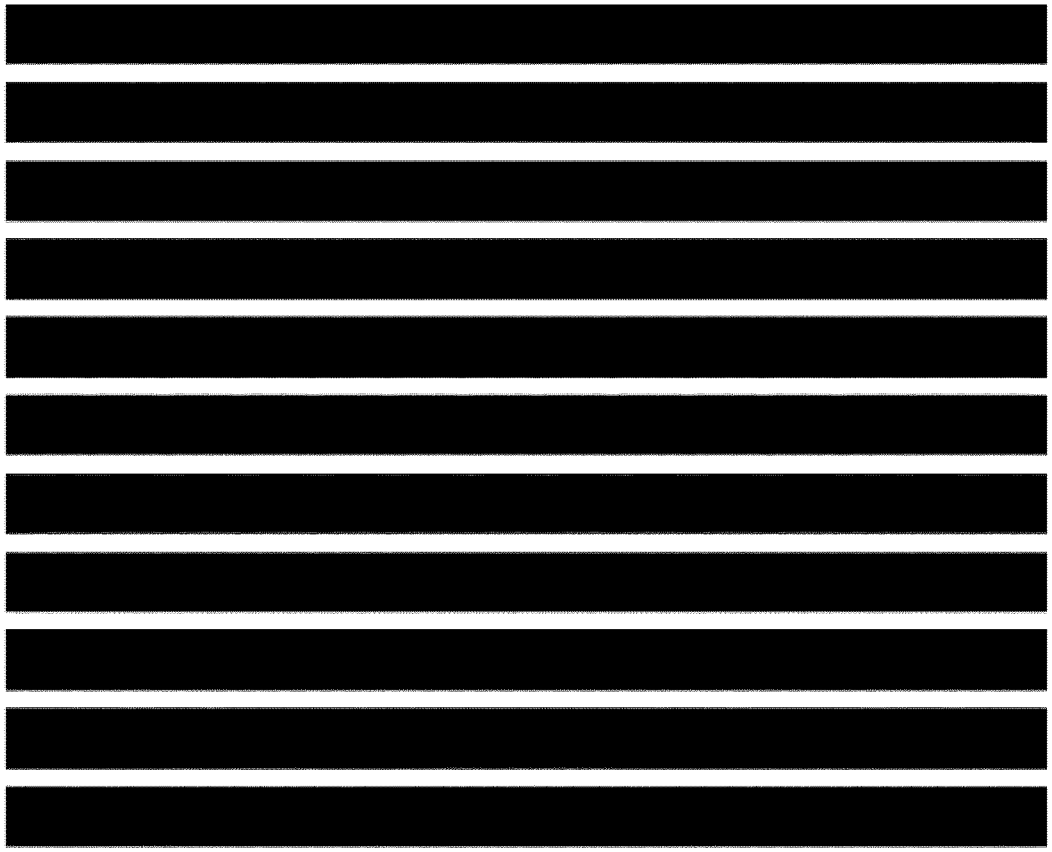
FIGS. 29-36 show schematic plan views indicating different recess (e.g. groove or hole) shapes for use in embodiments of the present invention.
Figure 30:
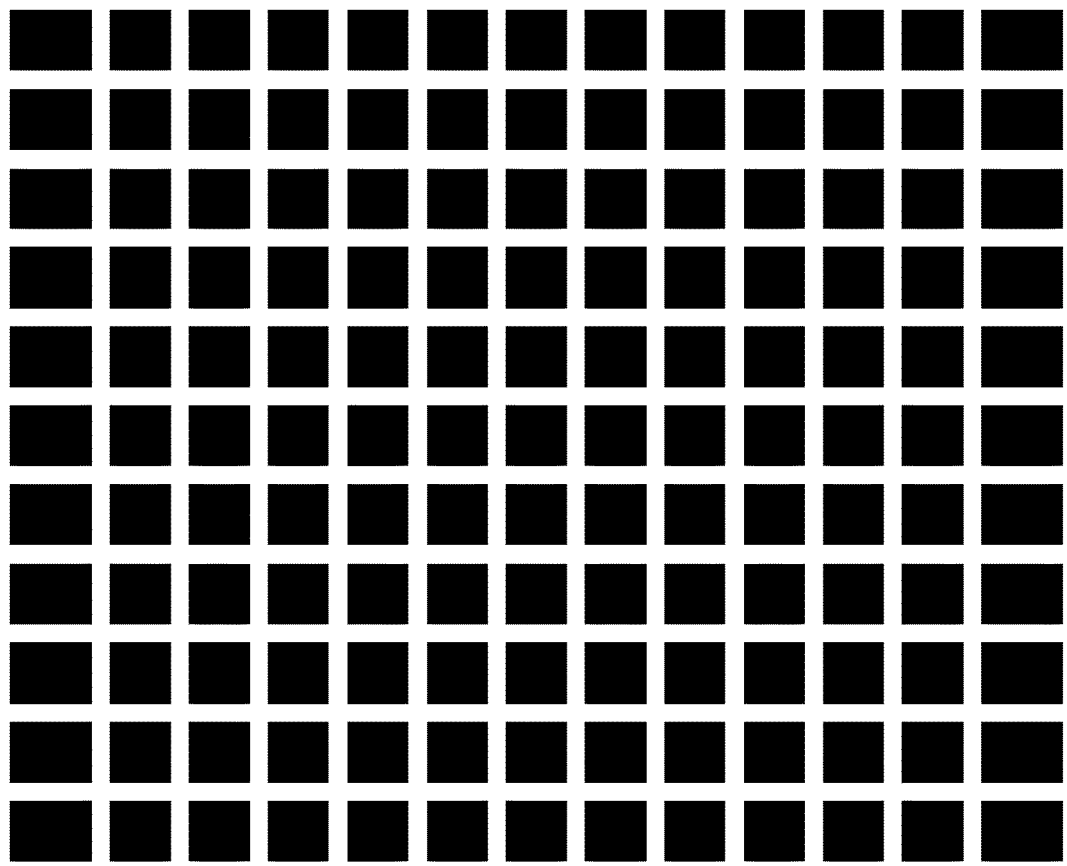
Figure 31:
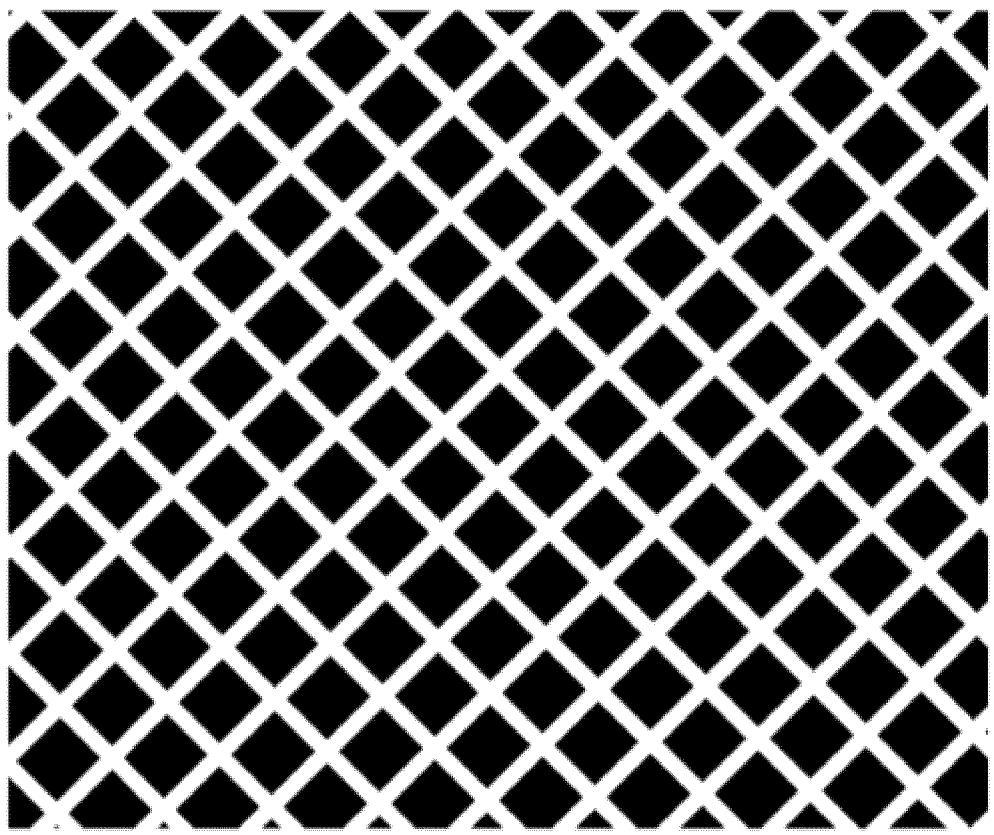
Figure 32:
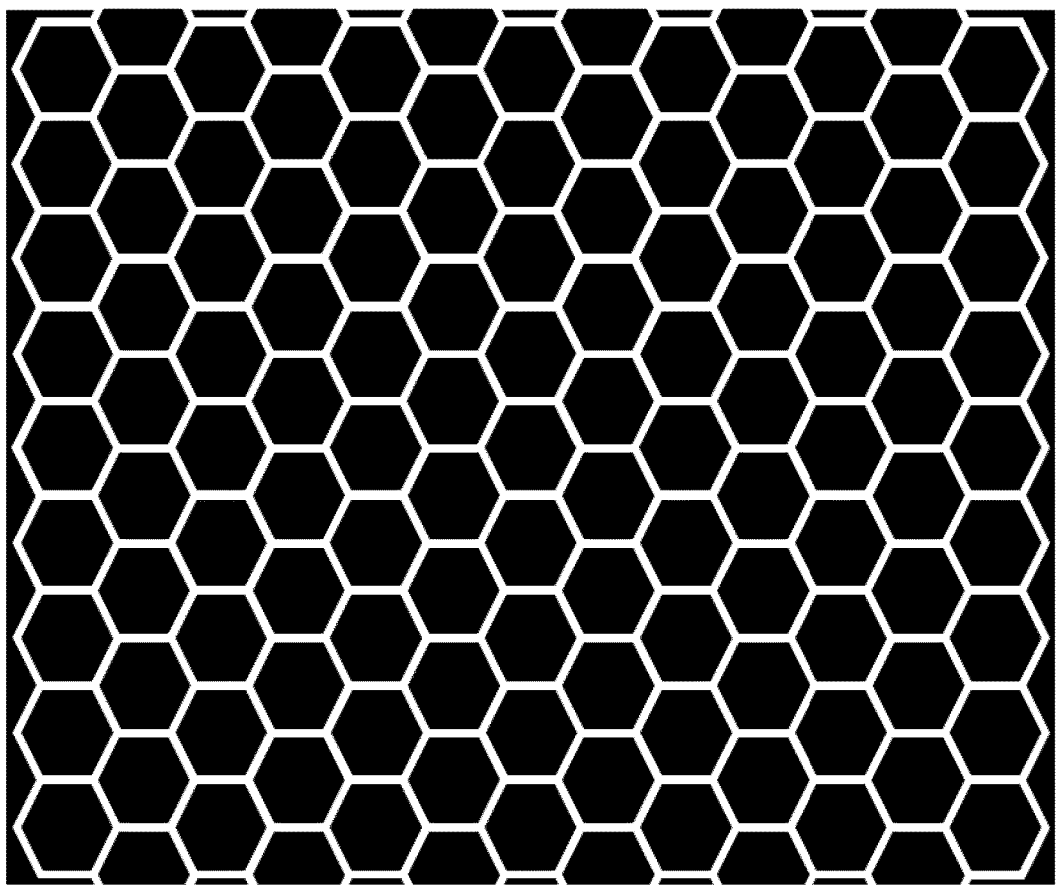
Figure 33:
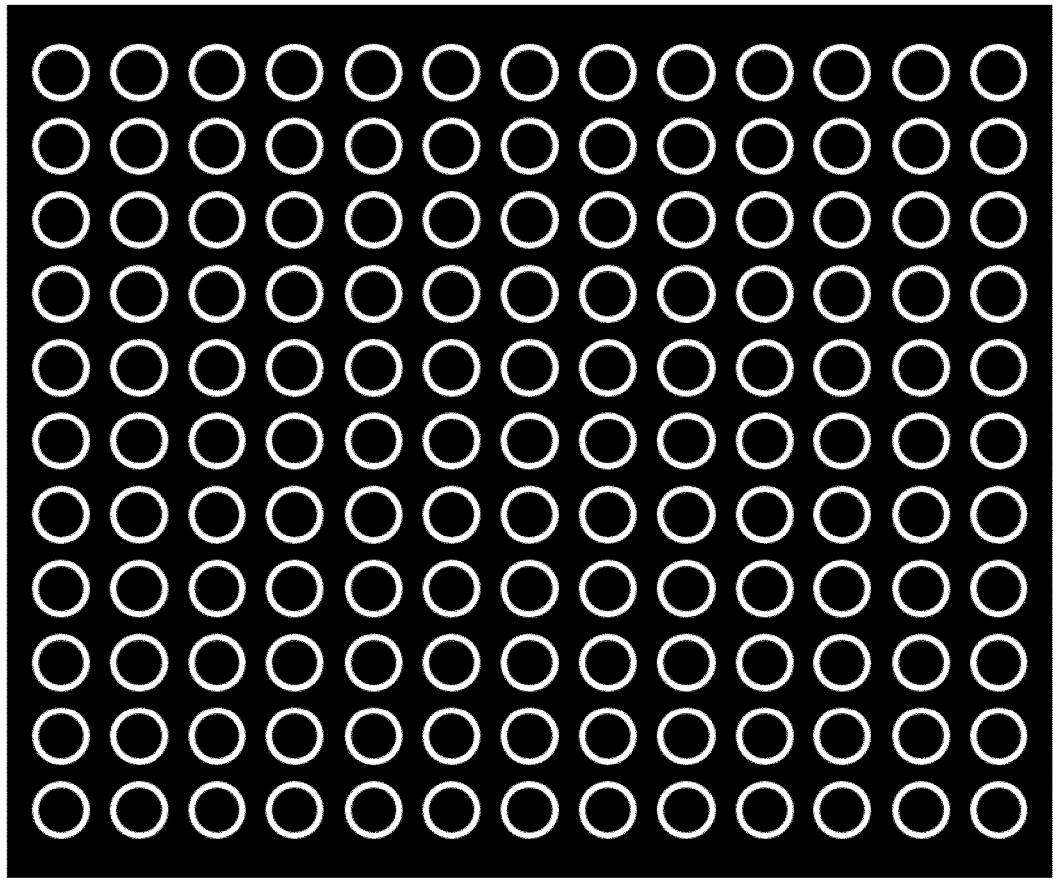
Figure 34:
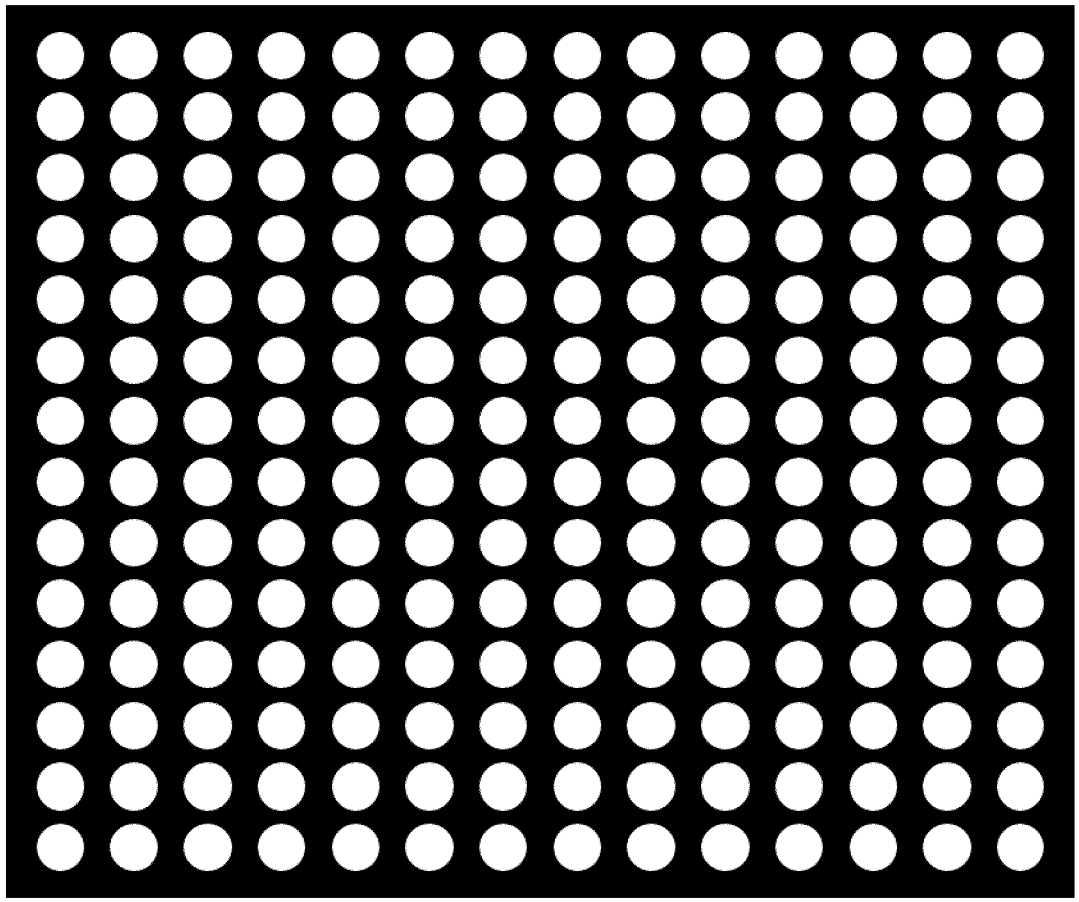
Figure 35:
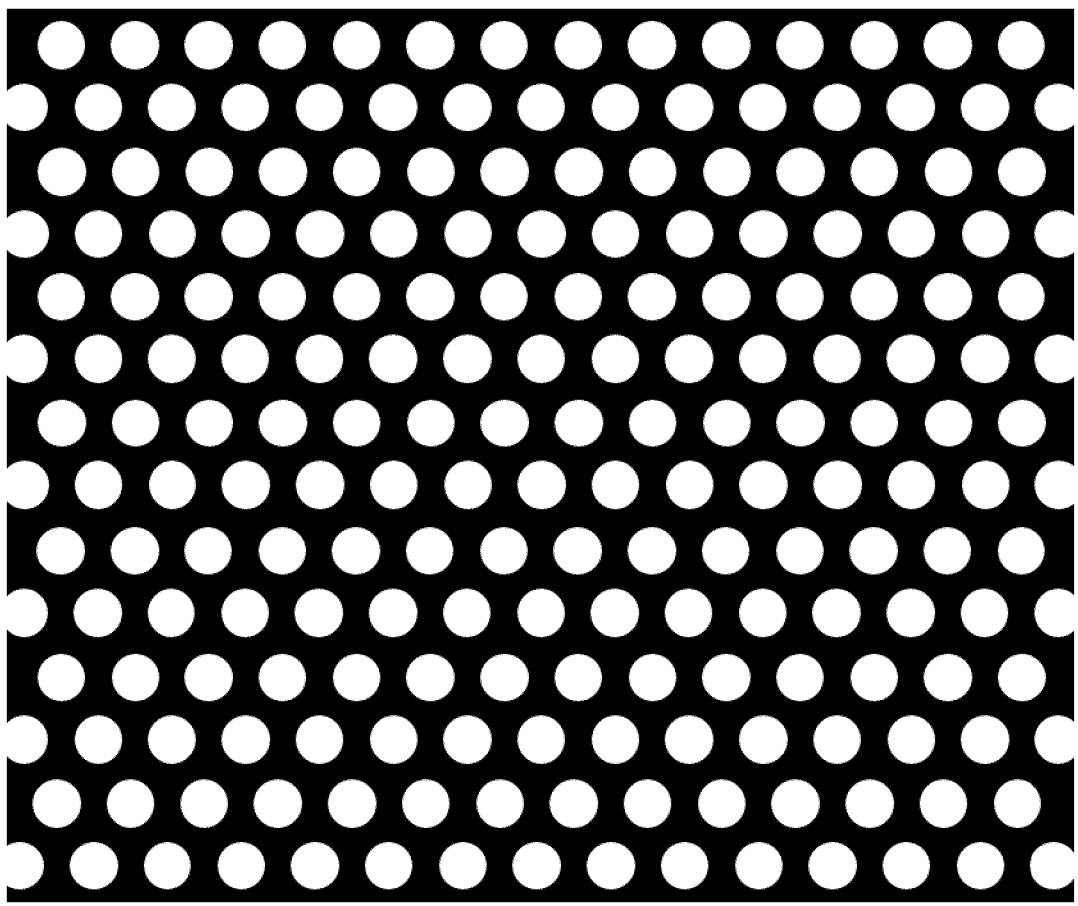
Figure 36:
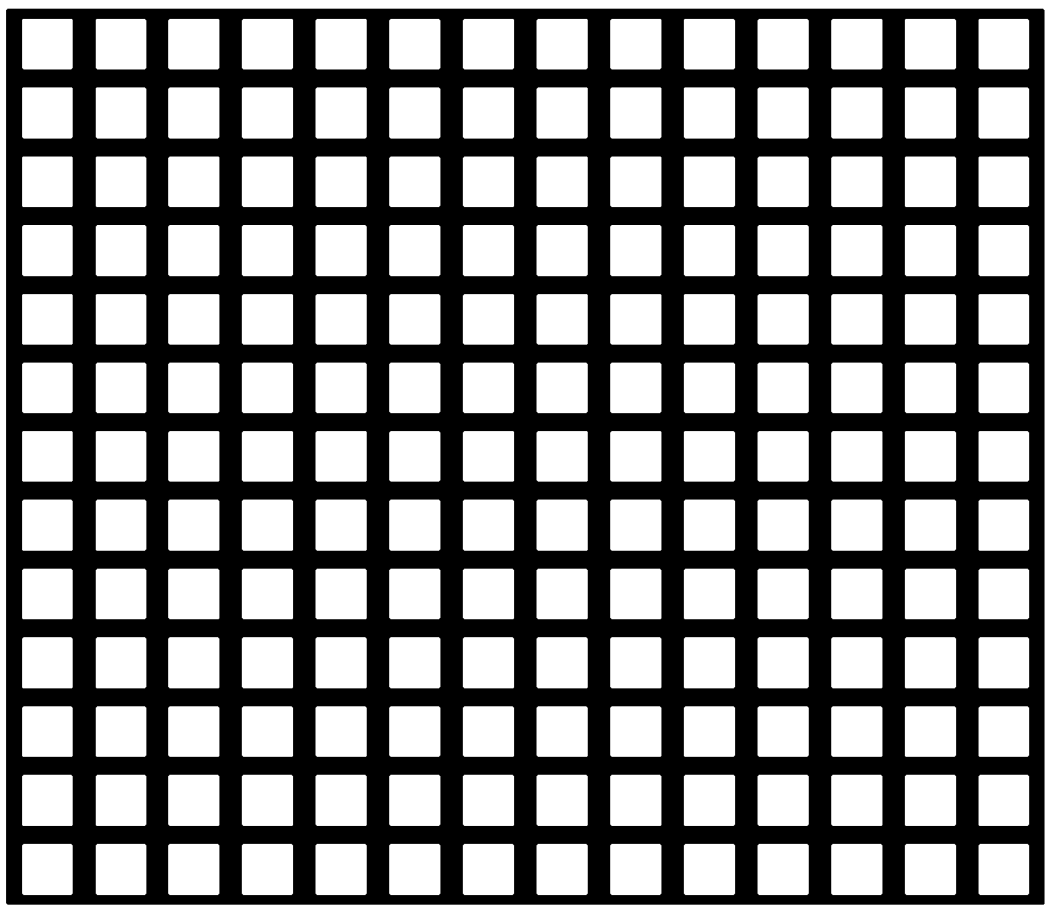

FIGS. 29-36 show schematic plan views indicating different recess (e.g. groove or hole) shapes for use in embodiments of the present invention. FIG. 29 shows an arrangement of parallel grooves (white lines) formed in a membrane (black background). FIGS. 30 and 31 show arrangements of interconnected rectilinear grooves. In these arrangements, an array of upstanding square islands are formed by the grooves. FIG. 32 shows arrays of grooves which form an array of upstanding hexagonal islands. FIG. 33 shows recesses in the form of small circular grooves arranged in a rectilinear lattice. FIG. 34 shows recesses in the form of small circular holes arranged in a rectilinear lattice. FIG. 35 shows recesses in the form of small circular holes arranged in a hexagonal lattice. FIG. 36 shows recesses in the form of small square holes arranged in a rectilinear lattice.

Experimental Results

In order to further describe the working of the present invention, experimental data is provided. These data demonstrate both the effects of forced convection, and the effects of the geometry of the present invention on flow invariance.

Some of these results are based on an experimental setup of the device as shown in FIG. 2, particular Sensor-4, and others are obtained using 2D Finite Element Modelling.

Forced Convection Measurements

For these measurements, a test jig was designed with mass flow controllers connected to a Keithley 2400 Source Meter for 4-wire resistance measurements. The mass flow controllers were controlled using Brokhorst Flow DDE, Flow View and Flow Plot software packages. All sensor signal control and measurement was carried out using LabTracer v2.9 software from Keithley. The sensor chip, as shown in FIG. 2, was placed in a DIL-16 ceramic package using a die attach and manual wire bonding machine. The area between the sensor chip and the package was then level flushed with an epoxy. A Plastruct Fineline CFS-6 plastic C-shaped channel was modified by attaching a thin transparency sheet using liquid poly from Humbrol, to create a complete duct for the test chamber. This was then attached over the exposed sensor using epoxy. The test chamber has cross sectional dimensions L×W of 3000 μm×700 μm and a total chamber length of 375 mm with distance to sensor from chamber edge of 300 mm.

The fluid channel provided a hydraulic diameter of 1.135 mm. In a worst case scenario flow rate of 1300 sccm yields a Reynolds number $Re_{air}$ of 1545 and $Re_{Argon}$ of 1852 at 27° C. Typically low Reynolds numbers (Re<2000) are classified as laminar flow. $Re_{Air}$ and $Re_{Argon}$ on therefore fall well within this limit.

In order to demonstrate the flow invariance of the embodiment of the invention shown in FIG. 2, a series of experiments were carried out relating to forced convection. Measurements were made using flow rates of 0 to 1300 sccm, in both air and argon. These flow rates correspond to inlet velocities of 0 to 21.4 ms$^{-1}$. Tests were carried out using gas supply directly from the mass flow controllers.

Figure 47:
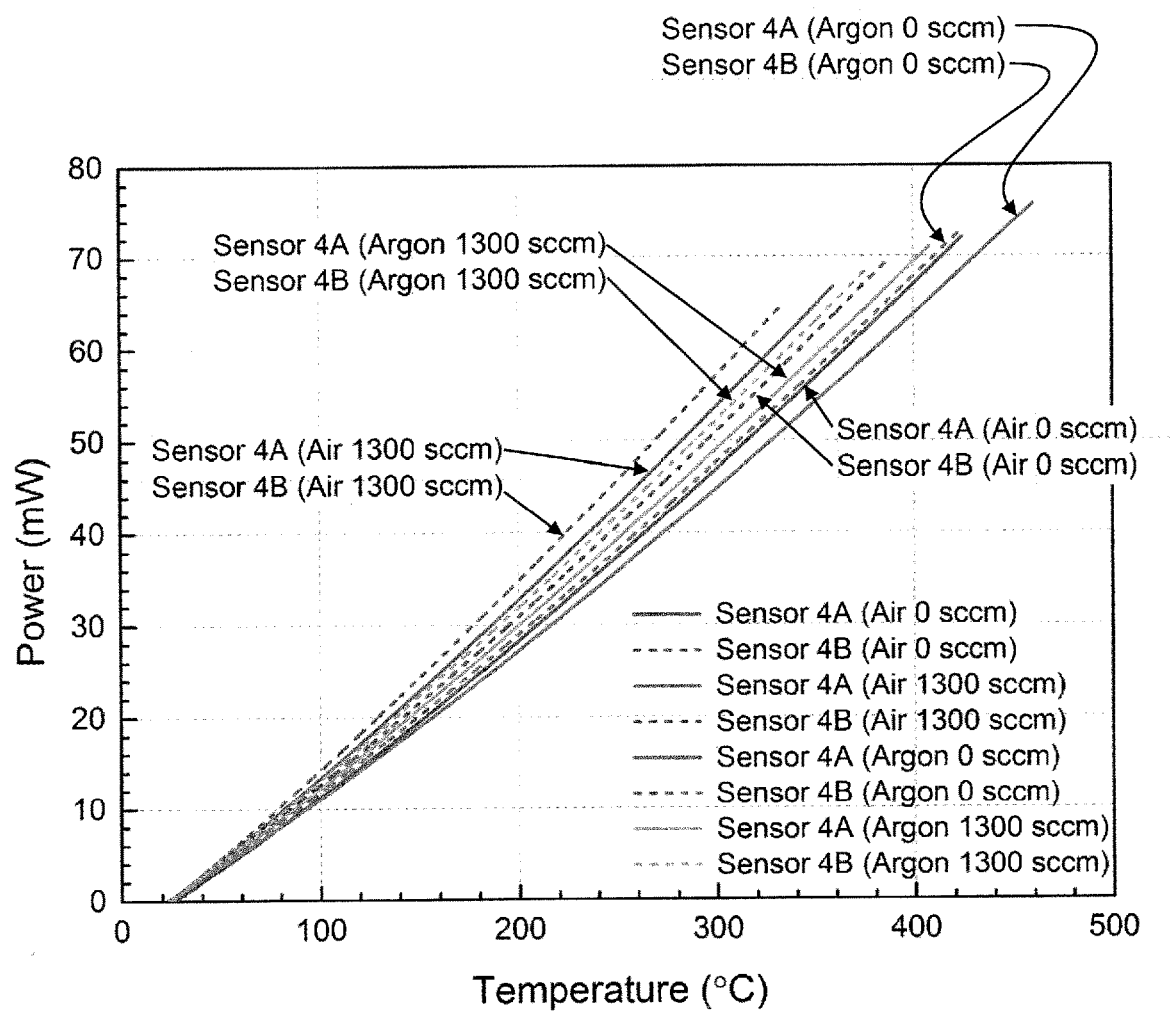
FIG. 47 shows the results of measurement of sensor temperature for Sensor-4A, Sensor-4B, Sensor-5A and Sensor-5B as a function of power delivered to the heaters of the device, depending on the composition (air or argon) of the gaseous environment and the flow rate.

FIG. 47 shows the variation of the power consumption of the heater with gas flow rate, with an input current of 40 mA, for both air and argon, and for both Sensor-4A and Sensor-4B. For gas flow rates of 0 sccm and 1300 sccm the difference in heater power loss and temperature for air and argon was 5.4 mW with 65.0° C. and 4.68 mW with 52.3° C. for sensor 4A' and also 4.81 mW with 53.3° C. and 4.2 mW with 47.13° C. for sensor 4B' respectively for a 40 mA current input. Both heaters show neither a constant power difference nor temperature difference. The difference in both parameters decreases for higher flow rates, and reduces overall for lower power consumption (i.e. lower current input).

Figure 37:
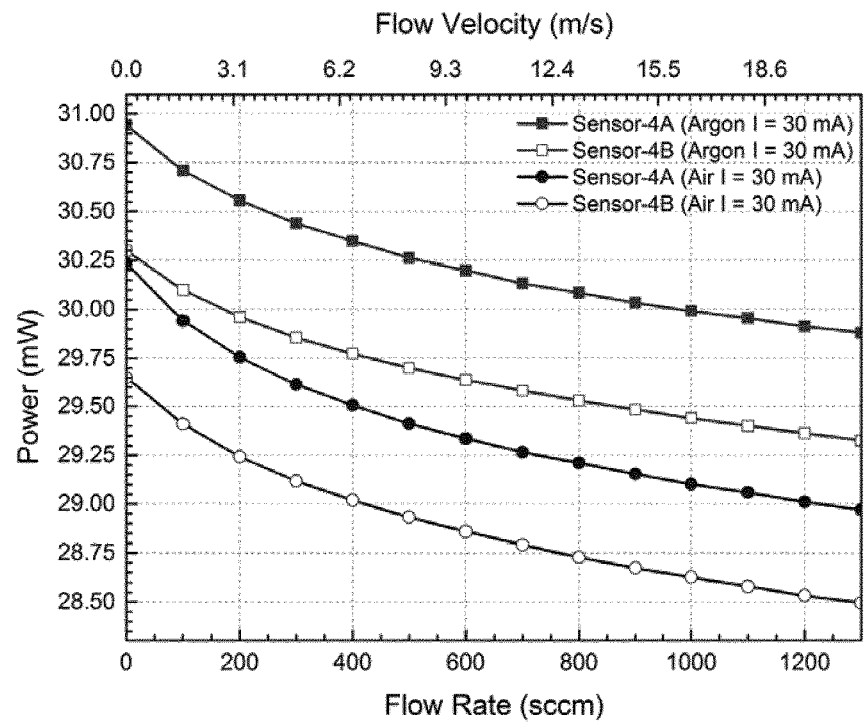
FIG. 37 shows the variation in heater power as a function of gas flow rate for air and argon for an embodiment of the invention.

Further experiments were done to study the power consumption curves as a function of flow rate for both sensors for both air and argon. The graph in FIG. 37 shows the results for a nominal 30 mA current input. Note that this is not intended to be a constant temperature operation but instead a constant nominal current operation. This experiment was done using a constant current source (set to inject 30 mA). As fluid flow increases the heater temperature drops due to forced convection. The resistive heater has a positive temperature coefficient of resistance. Therefore its resistance drops with temperature. Therefore the power also decreases. The power (P) loss is understood as $P=I^2R$, where I=current and R=resistance. The temperature values at 0 sccm flow and 1300 sccm flow are therefore different.

Figure 38:
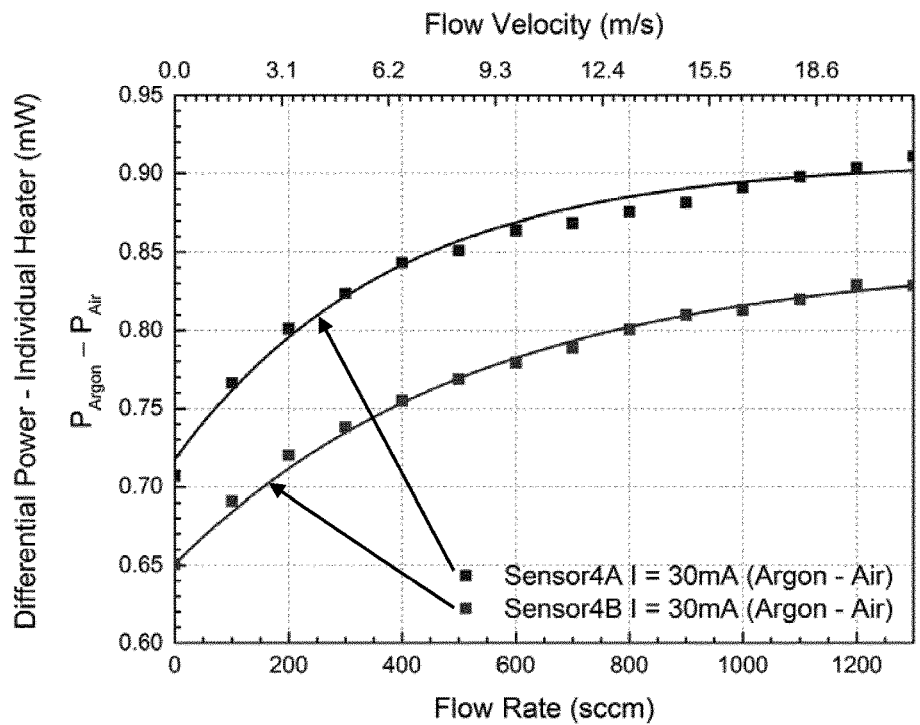
FIG. 38 shows the differential heater power as a function of gas flow rate, to demonstrate the effect of sensor geometry.

In FIG. 37, the curves appear to be parallel to each other, with different power levels for air and argon. All power curves reduce with increase in heat flow, showing the impact of forced convection leading to increased heat loss. However, the slope of the air curves are steeper than those for argon, particularly at lower flow rates. This is due to the differing material properties of the two gases, including density, dynamic viscosity, thermal conductivity, and specific heat capacity. To eliminate the effect of these material properties, FIG. 38 shows a differential measurement taken between air and argon. There is a variation in the slope of the two curves, which is more pronounced at the lower flow rates. Thus, geometry is shown to be playing a role which is directly related to groove width and depth.

Each curve in FIG. 38 corresponds to Sensor-4A and Sensor-4B individually. Furthermore, each curve is a differential measurement between argon and air for the same sensor. The exponential curve fitting lines over the measured data show a variation in the slope of the two curves. This difference is significant towards the low flow rate end as compared with the high flow rate side. Thus geometry is clearly playing a role which is directly related to the groove width and depth.

Figure 39:
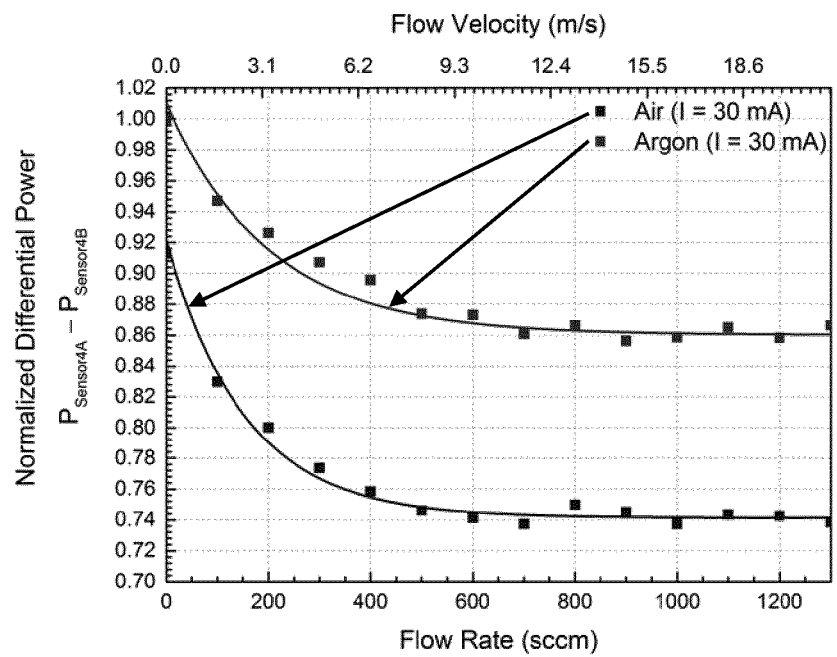
FIG. 39 shows the differential heater power between a grooved sensor, and a sensor without grooves for flow rates between 0 and 1300 sccm.
Figure 40:
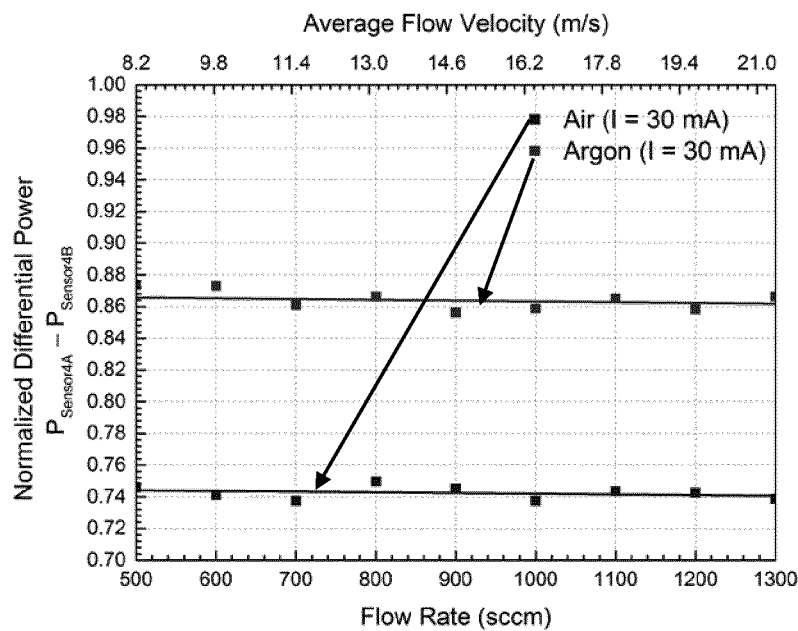
FIG. 40 shows the differential heater power between a grooved sensor, and a sensor without grooves for flow rates between 500 and 1300 sccm, being a portion of the results shown in FIG. 39.

FIGS. 39 and 40 show the dependence on flow rate of a differential measurement between Sensor-4A (without grooves) and Sensor-4B (with grooves). FIG. 40 shows the region of the graph with a flow rate between 500 and 1300 sccm, or between 8.2 and 21 $ms^{-1}$. Evidently, in this region the power differential between the two sensors remains substantially constant (shown by the substantially flat exponential trendline fitted onto the data), regardless of the flow rate of the gas. FIG. 40 therefore provides clear indication of the flow invariance of the device, at the given flow rates. Furthermore, since the lines for air and argon do not overlap, this demonstrates that the groove effectively changes the thermal conductivity of the membrane dependent on the nature of the gas molecules which are present.

Below 500 sccm (8.2 $ms^{-1}$) the power differential is not constant. This is because the thermal behaviour of the fluid below this point is highly non-linear. However, the "threshold" point at which the flow invariance becomes apparent can be varied by varying geometrical factors such as the depth of the groove, the width of the groove, geometrical 3D design of the groove, the height of the chamber itself and also the operating temperature of the heater.

2D FEM Simulation Analysis of Sensor 4B

In order to show the effects of a single groove on the streamlines of a gas flow, a 2D FEM model of a cross section of a groove of sensor 4B' was created. Since the difference in geometry between Sensor-4A and Sensor-4B is only in terms of the grooves, it is important to analyse the groove structure and the interaction of the fluid therewith. A number of parametric simulations were performed using an extremely fine mesh with boundary layers to account for fluid flow above rough surfaces especially within the grooves.

The parametric simulations included variation of the gas type (between air and argon) and also heater temperature, both as a function of flow velocity. The volumetric force effect based on gas density and the force of gravity on the gas molecules was also included. The flow was considered laminar for these experiments, and the total channel height above the sensor was fixed at 1000 μm.

Figure 41:
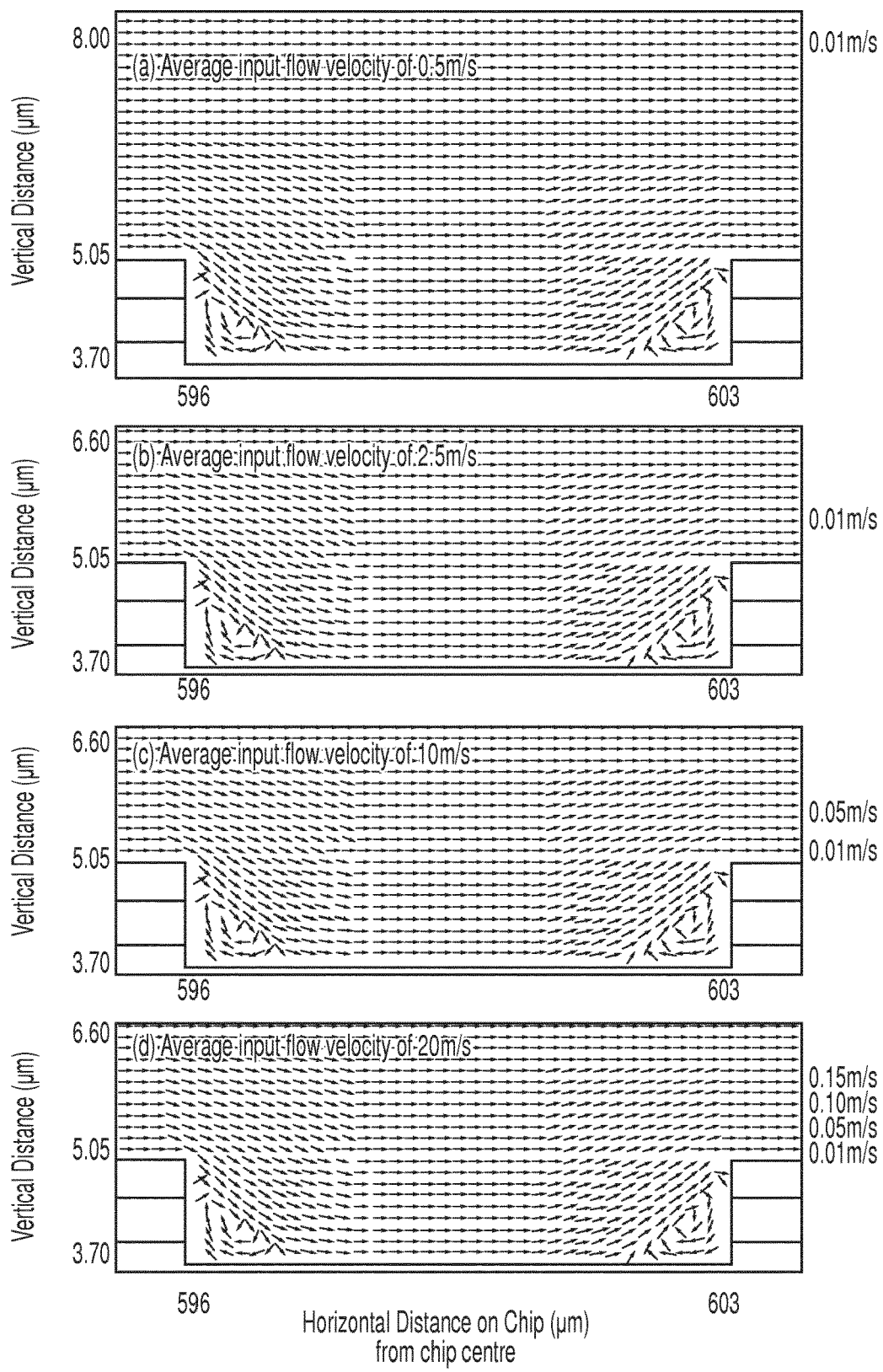
FIGS. 41(a)-(d) show constant velocity contours with air flow profile for a groove with dimensions 7 μm (length) by 1.35 μm (depth), in a 2D FEM simulation at 200° C. heater temperature with different average input flow velocity. Vertical distance is from the bottom of the membrane.

FIG. 41 shows the 2D results for the flow of air within a groove with dimensions 7 μm by 1.35 μm. The flow direction, from left to right, is perpendicular to the length of the groove (in to the plane). The flow arrows have been normalized in order to provide a clear direction of fluid flow. Velocity contours are also plotted. Based on experimental data of heater power consumption as a function of gas flow rate, it was assumed that below the 0.1 $ms^{-1}$ velocity contour, the flow of gas was insignificant in terms of changes in heater power consumption—i.e. there is no significant forced convective effect when the gas is moving at less than 0.1 $ms^{-1}$. Two observations can be made from FIGS. 41 (a) to (d):

There is vortex formation in the corners of the groove which forms a fluid "dead zone". Fluid in these "dead zones" can only be replaced by diffusion, as flow here has no effect.

The velocity contours show a sudden fall for changes in fluid inlet velocity from 0 to 10 $ms^{-1}$. After that, the 0.1 $ms^{-1}$ contour does not shift significantly further down. This shift reduces exponentially.

Figure 42:
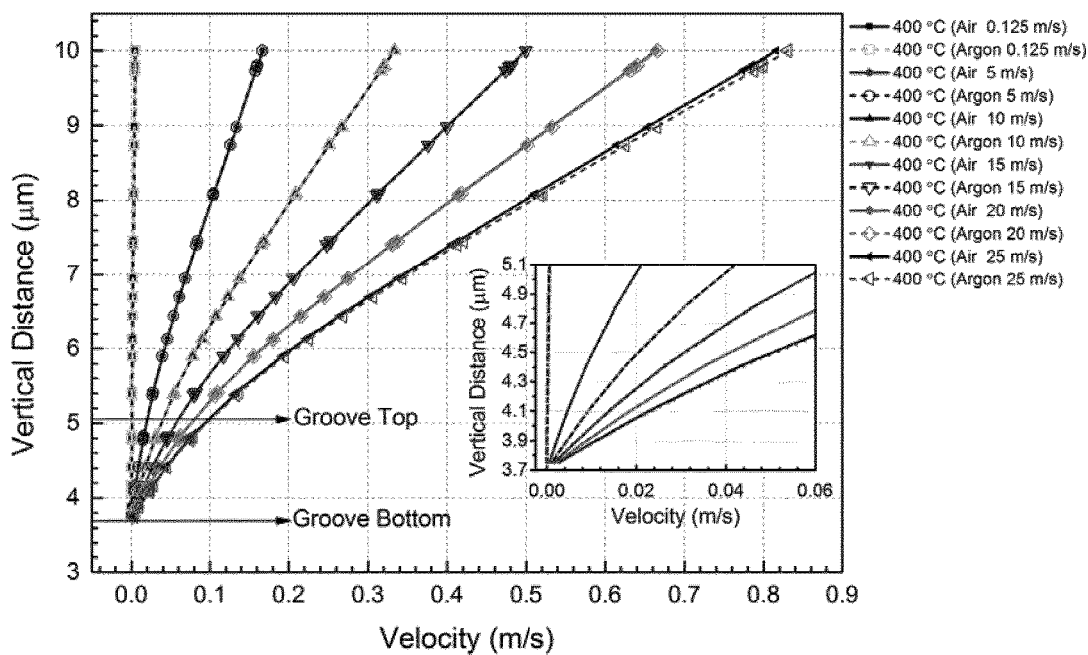
FIG. 42 shows inlet fluid velocity as a function of vertical distance for air and argon at 400° C. for an embodiment of the invention.

These two key observations were further studied by first analysing the horizontal velocity profile as a function of the vertical upward distance from the centre of the bottom of the groove. The centre point was chosen because this point would reflect the maximum change since dead zones are present at the inner groove edges as described earlier. This was studied for air and argon at a fixed heater temperature and for a range of inlet velocities as shown in FIG. 42. As observed from the inset in this figure the velocity profile as a function of vertical distance is hardly impacted by the nature of the gases studied within the groove volume. However, higher chamber inlet velocities do show a significantly large mass transport phenomenon occurring within the groove, where mass transport refers to bulk movement of the gas molecules due to forced convection-. This means that as the flow velocity is increased only a percentage of the gas filling the entire volume of the groove is actually stationary. The remaining gas is mass transported out of the groove. Thus, the effective thermal conductivity of the membrane keeps changing with flow velocity and makes the sensor increasingly sensitive to forced convection.

Figure 43:
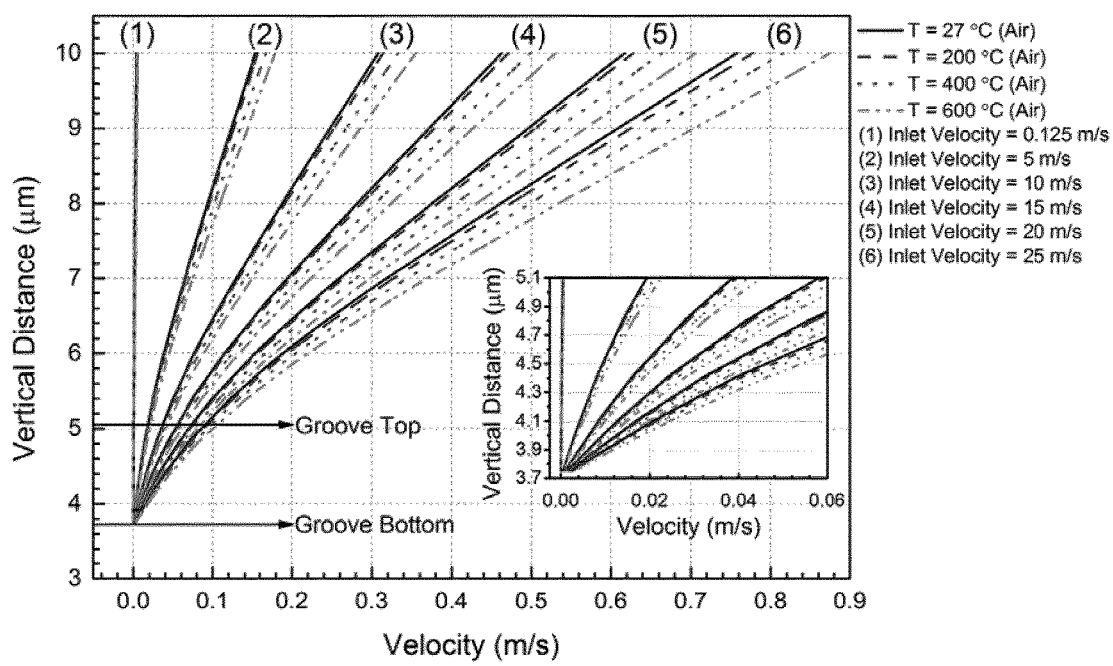
FIG. 43 shows inlet fluid velocity as a function of vertical distance for air at different temperatures for an embodiment of the invention.

Since within the groove the nature of the gas did not show a remarkable difference further analysis was done only using air but changing the temperature of the heaters. The results for this analysis are presented in FIG. 43. As the temperature increases the gaseous density, thermal conductivity, specific heat capacity and dynamic viscosity values change. Consequently the thermal diffusivity changes along with the respective Reynolds number, Prandtl number and Nusselt number values. These small changes are reflected by the shift in the velocity as a function of vertical distance within the groove as shown in the figure and highlighted in the provided inset. Consequently in the experimental measurements a shift towards a higher cut off inlet velocity was observed to achieve flow invariant sensor response i.e. the shift towards around 600 sccm as compared with 500 sccm flow rates for 40 mA current as compared with 30 mA current respectively.

Figure 44:
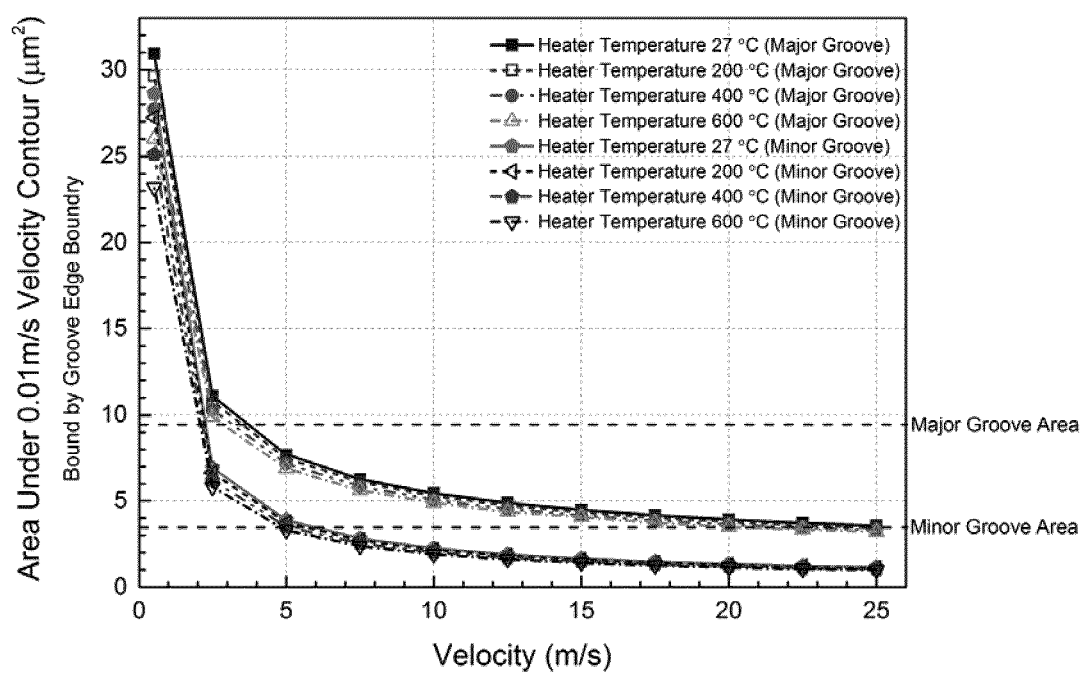
FIG. 44 shows the area under the 0.1 ms$^{-1}$ contour for major and minor grooves in air for an embodiment of the invention.

To analyse the extent of the flow invariance of the grooved Sensor-4B, the volume of gas underneath the 0.1 $ms^{-1}$ contour was considered across the full range of inlet velocities. On the fabricated sensor the grooves are not isolated continuous trenches along a single axis but rather form a connected network running perpendicular to each other. Thus for 2D simulation for volume analysis, only the grooves perpendicular to the flow of gas were considered. Furthermore, the length of the groove (i.e. with direction in to the plane) was considered infinite and the volume was translated to volume per unit length which equates to the cross sectional area. The results for this analysis are presented in FIG. 44. Both the major and minor grooves show an exponential drop in the area below the velocity contour of 0.1 $ms^{-1}$ as the gas flow begins to develop irrespective of the heater temperature. The exponential decay appears to saturate and flatten out towards higher inlet velocities. The major groove curve starts displacing air in the groove at approximately 3 ms$^{-1}$ inlet velocity while this occurs for the minor groove at around 5 ms$^{-1}$ inlet velocity. At 25 ms$^{-1}$ inlet velocity less than 50% of the fluid in both grooves is still stationary and trapped. It is noticeable that from 15 ms$^{-1}$ till 25 ms$^{-1}$ the change in fluid displaced area is 20% for the major groove whilst for the minor groove the same percentage displacement occurs from 17.5 ms$^{-1}$ till 25 ms$^{-1}$ inlet velocity. This is primarily due to the shallow depth of the groove as the width of both grooves is comparable (7 µm for major and 7.7 µm for minor). The 0.01 m/s flow contour, is to be understood as a reference line for explanation. A more stringent value can be selected if wanted, e.g. an order of magnitude less. It is considered that 0.01 m/s is a reasonable value which serves to explain the phenomenon of trapped gas molecules for this particular embodiment of the invention.

The heater temperature change shows a shift in the curve towards higher mass transport out of the groove at lower inlet velocities compared with higher inlet velocities. This is due to change of material properties with temperature. However, the cooling effect increases with higher inlet velocity and consequently the change in material properties is reduced. As mentioned above irrespective of the temperature the mass transport of fluid in the groove shows an exponential decay initially and then saturates. This can be justified by the following explanation, although the inventors do not wish to be bound by theory. When the fluid is under natural convection, i.e. when the gas is not flowing, the gas molecules are subject to Brownian motion and also density changes if the heater is at a higher temperature than the ambient environment. The major force acting on the particles is gravity. When forced convection initiates the gas molecules initially compress and then the entire bulk of them move together till the point that intermolecular attraction forces become weaker than the force due to forced convection. The exponential decay in the curve profile is observed till this point is reached. Then the inertia which had been building up finally takes over with gas particles slide across each other depending upon the force of friction each one faces due to its relative location next to the sensor surface or in the groove. At a further higher velocity value the vortices at the edges of the grooves permanently lock in some percentage of the gas while the velocity stream lines keep on compressing against each other without removal of significantly additional gas molecules. This corresponds to the saturation part of the curve achieved at higher velocities.

Optimization of the Sensor-4B

This section builds on the experimental results from the previous section in order to establish the features of the sensor which enable flow invariant measurements with a wider range of inlet velocities. In particular the height of channel 2 (the height of the duct through which the gas flows, being measured as the direct vertical distance from the top surface of the sensor without grooves to the duct ceiling) and the width of the grooves are varied.

Figure 45:
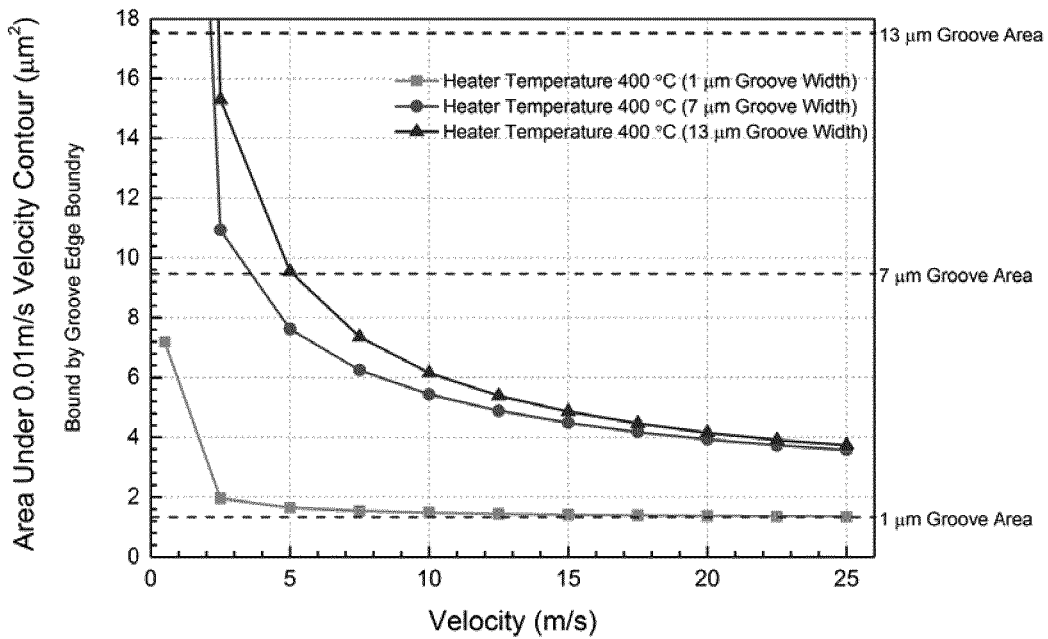
FIG. 45 shows the area under the 0.1 ms$^{-1}$ contour for varying groove width according to embodiments of the invention.

For the analysis of groove width, the height of the test chamber was kept constant at 1000 µm. This falls under the minichannel regime classified by Kandlikar, S. G. et al (2006). The Navier-Stokes equations with no slip boundary conditions were used at all solid-fluid interfaces for the upper fluidic test chamber. The results of this analysis are presented in FIG. 45. It is observed that as the groove width is reduced the formation of vortices to trap the gas particles in the grooves becomes significantly stronger and the ability of the gas flowing in the chamber to penetrate the grooves by forced convection is eliminated. Groove width of 1 µm shows that the area under the curve corresponding to 0.1 ms$^{-1}$ velocity contour does not breach the 1 µm groove area even at 25 ms$^{-1}$ inlet velocity. The flatness of the curve means that Sensor-4B with a groove of extremely small widths in conjunction with Sensor-4A can act as being fully flow invariant.

Figure 46:
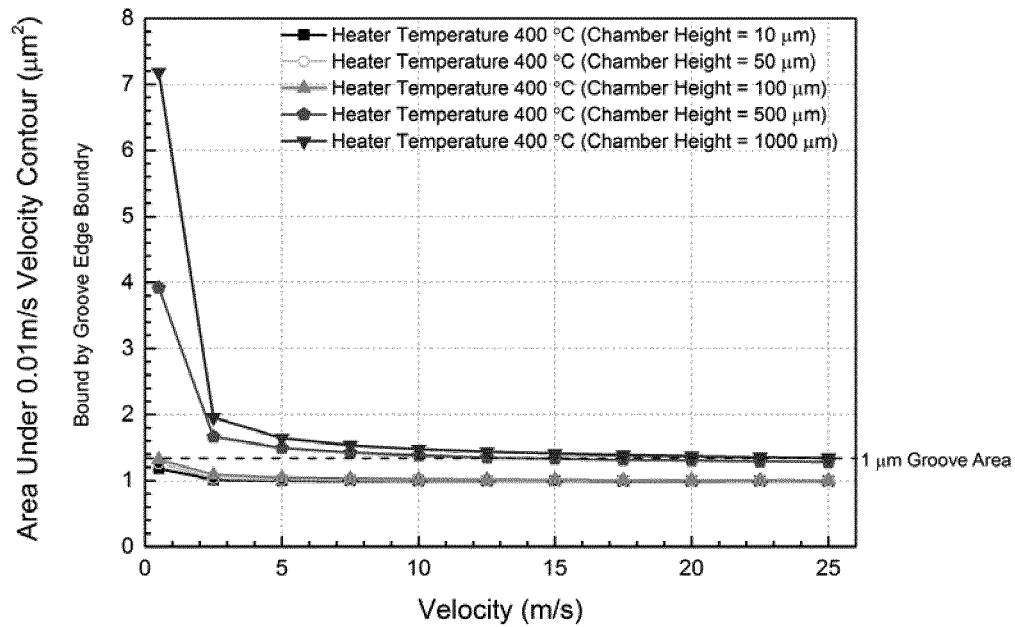
FIG. 46 shows the area under the 0.1 ms$^{-1}$ contour for varying channel height.

For analysis of sensor performance as a function of chamber height it was necessary to incorporate slip boundary condition for 100 µm, 50 µm and 10 µm chamber heights. This is because as the chamber height is reduced the Knudsen number increases and the fluid flow moves from continuum flow to slip flow. Knudsen number is a dimensionless number that defines the ratio of the molecular mean free path length to a representative physical length scale (the characteristic chamber length in this case). In this scenario the Navier-Stokes equations remain applicable, provided a velocity slip and a temperature jump are taken into account at the walls. The results of this analysis are presented in FIG. 46. The sensor behaviour becomes almost completely flow invariant as the chamber height is reduced but at a loss of some fluid being permanently removed from the groove. This occurs mainly for 50 µm and 10 µm channels and also for 100 µm channel but to a lesser degree. On the other hand if the groove width is made large and the chamber height is reduced then due to slip flow even the vortices at the edges are effected yielding poorer performance. Thus the combination of a small chamber height, small groove width, deeper grooves and higher number of total grooves should provide a better flow invariant performance.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

LIST OF NON-PATENT DOCUMENT REFERENCES

Thermal conductivity gauge XEN-TCG3880 of Xensor Integration by (Distributieweg 28, 2645 EJ Delfgauw, Netherlands, www.xensor.nl)

B. C. Kaanta, H. Chen, X. Zhang, "Novel device for calibration-free flow rate measurements in micro gas chromatographic systems", J. Micromech. Microeng. 20 (2010) 095034 (7 pp)

B. C. Kaanta, H. Chen, X. Zhang, "Effect of forced convection on thermal distribution in micro thermal conductivity detectors", J. Micromech. Microeng. 21 (2011) 045017 (8 pp)

F. Rastrello, P. Placidi, A. Scorzoni, "Thermal Conductivity Detector for Gas-Chromatography: Acquisition System and Experimental Measurements", Instrumentation and Measurement Technology Conference (2012) IEEE International, pp. 1226-1230

F. Rastrello et al., "Thermal Conductivity Detector for Gas Chromatography: Very Wide Gain Range Acquisition System and Experimental Measurements", IEEE Transactions on Instrumentation and Measurement vol. 62, no. 5, 2013

D. F. Reyes Romero, K. Kogan, A. S. Cubucku, G. A. Urban, "Simultaneous flow and thermal conductivity measurement of gases utilizing a calorimetric flow sensor", Sensors and Actuators A, 203 (2013), 225-233

Sarfraz, S.; Kumar, R. V.; Udrea, F., "A dual mode SOI CMOS MEMS based thermal conductivity and IR absorption gas sensor," SENSORS, 2013 IEEE , vol., no., pp. 1, 4, 3-6 Nov. 2013

Brand, O. and G. K. Fedder, CMOS—MEMS. 1st ed. 2008: Wiley-VCH, Weinheim. 596 Agilent SI-02239 490 Micro GC Solution Data Sheet. 2010

Sparkman, O. D., Z. E. Penton, and F. G. Kitson, Gas Chromatography and Mass Spectrometry: A Practical Guide. 2nd ed. 2011: Elsevier Sze, S. M., Semiconductor Sensors. 1994: John Wiley & Sons, Inc. 576

Sevcik, J., Detectors in Gas Chromatography. 1976: Elsevier. 192

Chemical Weapons Convention Chemical Analysis. 2005: John Wiley & Sons, Ltd. 462

Mcnair, H. M. and J. M. Miller, Basic Gas Chromatography. 2nd ed. 2009: John Wiley & Sons, Inc.

Kaanta, B. C., et al., Temperature distribution on thermal conductivity detectors for flow rate insensitivity. Sensors and Actuators A: Physical, 2011. 167(2): p. 146-151

Ali, S. Z., et al., Tungsten-Based SOI Microhotplates for Smart Gas Sensors. Microelectromechanical Systems, Journal of, 2008. 17(6): p. 1408-1417

Haneef, I., SOI CMOS MEMS Flow Sensors. 2009, PhD Thesis, University of Cambridge, UK Kandlikar, S. G. et al. "Heat transfer and Fluid Flow in Minichannels and Microchannels." 2006: Elsevier. 450

The invention claimed is:

1. A thermal conductivity sensing device for use in sensing one or more gaseous components in a flowing gaseous environment, the device having a first sensor and a second sensor for exposure to the gaseous environment, each sensor providing a surface for thermal contact with the gaseous environment, each sensor providing an output relating to heat transfer between said surface and the gaseous environment, the first sensor having an associated flow altering means to affect gas flow at least at part of said surface of the first sensor, to be different to gas flow at the surface of the second sensor, the device being operable to compare outputs of the first and second sensors,
   wherein the first and second sensors are provided with respective heating elements, and
   wherein each respective heating element is embedded in a membrane structure which provides the surface for thermal contact with the gaseous environment, the heating element having electrical contacts for providing electrical power to the heater with the membrane structure supported on a silicon or SOI substrate.

2. The thermal conductivity sensing device according to claim 1, wherein at least one of the heating elements is made of tungsten or a tungsten-based alloy.

3. The thermal conductivity sensing device according to claim 1, wherein the first and second sensors are for location in a channel having a wall which opposes the sensor surface wherein the distance between the sensor surface and the channel wall is at most 10000 µm.

4. The thermal conductivity sensing device according to claim 1, wherein the first and second sensor are substantially identical, with the exception of the flow altering means.

5. The thermal conductivity sensing device according to claim 1, wherein the device is manufactured using a MEMS only process.

6. The thermal conductivity sensing device according to claim 1, wherein the flow altering means includes at least one recess in the surface of the first sensor.

7. The thermal conductivity sensing device according to claim 6, wherein a plurality of recesses is provided.

8. The thermal conductivity sensing device according to claim 6 wherein the recess is a groove.

9. The thermal conductivity sensing device according to claim 8, wherein the device has a plurality of grooves.

10. The thermal conductivity sensing device according to claim 9, wherein at least some of the grooves are parallel to each other.

11. The thermal conductivity sensing device according to claim 1, wherein the device is manufactured using a CMOS process and/or a SOI process.

12. The thermal conductivity sensing device according to claim 11 incorporating an infrared emitter.

13. The thermal conductivity sensing device according to claim 11 incorporating a flow sensor.

14. A method for measuring the thermal conductivity of one or more gaseous components in a flowing gaseous environment, the method including:
   exposing a surface of a first sensor to the flowing gaseous environment, for thermal contact between the first sensor and the gaseous environment;
   generating a first output relating to heat transfer between said surface of the first sensor and the gaseous environment;
   exposing a surface of a second sensor to the same flowing gaseous environment, for thermal contact between the second sensor and the gaseous environment;
   generating a second output relating to heat transfer between said surface of the second sensor and the gaseous environment;
   comparing the outputs of the first and second sensors;
   wherein the first sensor has an associated flow altering means to affect gas flow at least at part of said surface of the first sensor, to be different to gas flow at the surface of the second sensor,
   wherein the first and second sensors are provided with respective heating elements, and
   wherein each respective heating element is embedded in a membrane structure which provides the surface for thermal contact with the gaseous environment, the heating element having electrical contacts for providing electrical power to the heater with the membrane structure supported on a silicon or SOI substrate.

15. A system for performing gas chromatography, the system including:
   a separation column with a gas inlet and a gas outlet, the separation column being provided with a stationary phase, and
   a thermal conductivity sensing device for use in sensing one or more gaseous components in a flowing gaseous environment, the device having a first sensor and a second sensor for exposure to the gaseous environment, each sensor providing a surface for thermal contact with the gaseous environment, each sensor providing an output relating to heat transfer between said surface and the gaseous environment, the first sensor having an associated flow altering means to affect gas flow at least at part of said surface of the first sensor, to be different to gas flow at the surface of the second sensor, the device being operable to compare outputs of the first and second sensors, wherein the thermal conductivity sensing device is adapted to receive a gas flow from the outlet of the separation column, wherein the first and second sensors are provided with respective heating elements, and wherein each respective heating element is embedded in a membrane structure which provides the surface for thermal contact with the gaseous environment, the heating element having electrical contacts for providing electrical power to the heater with the membrane structure supported on a silicon or SOI substrate.

16. A method of carrying out gas chromatography, the method including the steps:

separating one or more gas components from a gas carrier mobile phase using a separation column;

directing a gas flow from the outlet of the separation column to a thermal conductivity sensing device, the device having a first sensor and a second sensor for exposure to a gaseous environment, each sensor providing a surface for thermal contact with the gaseous environment, each sensor providing an output relating to heat transfer between said surface and the gaseous environment, the first sensor having an associated flow altering means to affect gas flow at least at part of said surface of the first sensor, to be different to gas flow at the surface of the second sensor, wherein the first and second sensors are provided with respective heating elements, and wherein each respective heating element is embedded in a membrane structure which provides the surface for thermal contact with the gaseous environment, the heating element having electrical contacts for providing electrical power to the heater with the membrane structure supported on a silicon or SOI substrate; and comparing the outputs of the first and second sensors of the thermal conductivity sensing device.

* * * * *